(12) United States Patent
Young et al.

(10) Patent No.: US 7,049,409 B2
(45) Date of Patent: May 23, 2006

(54) HEREGULIN-LIKE FACTOR ANTIBODIES

(75) Inventors: Paul E. Young, Gaithersburg, MD (US); C. Richter King, Washington, DC (US); Mia Hijazi, Washington, DC (US); Steven M. Ruben, Brookeville, MD (US)

(73) Assignees: Human Genome Sciences, Inc., Rockville, MD (US); Georgetown University Medical Center, Washington, DC (US)

( * ) Notice: Subject to any disclaimer, the term of this patent is extended or adjusted under 35 U.S.C. 154(b) by 279 days.

(21) Appl. No.: 10/609,370

(22) Filed: Jul. 1, 2003

(65) Prior Publication Data
US 2004/0048295 A1 Mar. 11, 2004

Related U.S. Application Data

(62) Division of application No. 09/097,681, filed on Jun. 16, 1998, now Pat. No. 6,727,077.

(60) Provisional application No. 60/049,942, filed on Jun. 17, 1997.

(51) Int. Cl.
*C07K 16/00* (2006.01)
(52) U.S. Cl. ............... 530/387.1; 530/387.3; 530/389.1; 530/388.1
(58) Field of Classification Search ............ 424/130.1; 530/387.1, 387.3, 389.1, 388.1
See application file for complete search history.

(56) References Cited

U.S. PATENT DOCUMENTS

| | | | |
|---|---|---|---|
| 6,096,871 A | 8/2000 | Presta et al. | |
| 6,121,415 A * | 9/2000 | Godowski et al. | ........... 530/324 |
| 6,252,051 B1 | 6/2001 | Godowski et al. | |

FOREIGN PATENT DOCUMENTS

WO  WO-99/02681 A9  1/1999

OTHER PUBLICATIONS

Coligan et al. Current Protocols in Immunology, 1991, John Wiley & Sons, USA, pp. 2.1.2-2.1.22.*
Hillier et al., "yn72d05.r1 Soares adult brain N2b5HB55Y Homo sapiens cDNA clone IMAGE:173961 5' similar to SP:A43273 A43273 Heregulin-Alpha Precursor-;contains LTR7 repetitive element ;, mRNA sequence," Database EMBL 'Online' Accession No. H23651 (Jul. 8, 1995).
Lewis et al., "Growth Regulation of Human Breast and Ovarian Tumor Cells by Heregulin: Evidence for the Requirement of ErbB2 as a Critical Component in Mediating Heregulin Responsiveness," *Cancer Res.*, 56:1457-1465 (Mar. 1996).
Zhang et al., "Neuregulin-3 (NRG3): A novel neural tissue-enriched protein that binds and activates ErbB4," *PNAS USA*, 94:9562-9567 (Sep. 1997).
Holmes et al., "Identification of Hereguln, a Specific Activator of p185erbB2," *Science*, 256:1205-1210 (May 22, 1992).
George et al., "Macromolecular Sequencing and Synthesis: Selected Methods and Application," Schlesinger, D.H. (eds.), Alan R. Liss, Inc., New York, NY, pp. 127-149 (1988).
Wilson, R.K., "The WashU-Merck EST Project," GenBank Accession No. H50042 (Sep. 18, 1995).
Wilson, R.K., "The WashU-Merck EST Project," GenBank Accession No. H49100 (Sep. 18, 1995).
Wilson, R.K., "The WashU-Merck EST Project," GenBank Accessoin No. H23651 (Jul. 6, 1995).
Culouscou et al., "Characterization of a breast cancer cell differentiation factor that specifically activates the HER4/P180ERB4 receptor," *J. Biol. Chem.*, 268(25):18407-18410 (1993).
Garraway et al., "Neuregulin-2, a new ligand of Erb3/Erb4-receptor tyrosine kinase," *Nature*, 387:512-516 (1997).
Gassmann et al. "Aberrant neural and cardiac development in mice lacking the ErB4 neuregulin receptor," *Nature*, 378(6555):390-394 (1995).
Hijazi et al. "NRG-3 in human breast cancers: Activation of multiple erbB family proteins," *Int'l J. Oncology*, 13(5):1061-1067 (1998).
Laverriere et al. "GATA-4/5/6, a subfamily of three transcription factors transcribed in developing heart and gut," *J. Biol. Chem.*, 269(37):23177-23184 (1994).

(Continued)

*Primary Examiner*—Gary Nickol
*Assistant Examiner*—Sean Aeder
(74) *Attorney, Agent, or Firm*—Human Genome Sciences, Inc.

(57) ABSTRACT

The present invention relates to a novel HLF protein which is a member of the heregulin family. In particular, isolated nucleic acid molecules are provided encoding the human HLF protein. HLF polypeptides are also provided as are vectors, host cells and recombinant methods for producing the same. The invention further relates to screening methods for identifying agonists and antagonists of HLF activity. Also provided are diagnostic methods for detecting disorders of the regulation of cell growth and therapeutic methods for treating disorders of the regulation of cell growth.

20 Claims, 6 Drawing Sheets

OTHER PUBLICATIONS

Plumb et al., "Human DNA sequence from clone RP1-185K11," Database EMBL 'Online' Accession No. AL136085 (Jan. 7, 2000).

Bowie et al., "Deciphering the Message in Protein Sequences: Tolerence to Amino Acid Substitutions," *Science*, 247:1306-1310 (1990).

Lazar et al., "Transforming Growth Factor Alpha: Mutation Aspartic Acid 47 and Leuine 48 Results in Different Biological Activities," *Molec. and Cell. Biol.*, 8:1247-1252 (1988).

Burgess et al., "Possible Dissociation of the Heparin-binding and Mitogenic Activities of Heparin-binding Growth Factor-1 from Its Receptor-binding Activities by Site-directed Mutagenesis of a Single Lysine Residue," *J. Cell. Biol.*, 111:2129-2138 (1990).

Bork, P., "Powers and pitfalls in sequence analysis," *Genome Res.*, 10:398-400 (2000).

* cited by examiner

Figure 1A
Her gulin-like Factor

```
  1 CTCTTCTTCCTCCTCCGCTACCACCACCACACCAGAAACTAGCACCAGCCCCAAATTTCA   60
  1 S  S  S  S  A  T  T  T  T  P  E  T  S  T  S  P  K  F  H       20

61 TACGACGACATATTCCACAGAGCGATCCGAGCACTTCAAACCCTGCCGAGACAAGGACCT  120
 21 T  T  T  Y  S  T  E  R  S  E  H  F  K  P  C  R  D  K  D  L    40

121 TGCATACTGTCTCAATGATGGCGAGTGCTTTGTGATCGAAACCCTGACCGGATCCCATAA  180
 41 A  Y  C  L  N  D  G  E  C  F  V  I  E  T  L  T  G  S  H  K    60

181 ACACTGTCGGTGCAAAGAAGGCTACCAAGGAGTCCGTTGTGATCAATTTCTGCCGAAAAC  240
 61 H  C  R  C  K  E  G  Y  Q  G  V  R  C  D  Q  F  L  P  K  T    80

241 TGATTCCATCTTATCGGATCCAAACCACTTGGGGATTGAATTCATGGAGAGTGAAGAAGT  300
 81 D  S  I  L  S  D  P  N  H  L  G  I  E  F  M  E  S  E  E  V   100

301 TTATCAAAGGCAGGTGCTGTCAATTTCATGTATCATCTTTGGAATTGTCATCGTGGGCAT  360
101 Y  Q  R  Q  V  L  S  I  S  C  I  I  F  G  I  V  I  V  G  M   120

361 GTTCTGTGCAGCATTCTACTTCAAAAGCAAAAGGAATATTACAGCAAATTCTGTGTCTGA  420
121 F  C  A  A  F  Y  F  K  S  K  R  N  I  T  A  N  S  V  S  E   140

421 GGAAAGATGGAAGGGTCTGCCTTCCCAGGAGCCCAATCTGCAACAAGACAAATAATGCCT  480
141 E  R  W  K  G  L  P  S  Q  E  P  N  L  Q  Q  D  K            160

481 AACAATGGATTAATGATGTCTACTATTCTGCAACTTACATCTCATTTCTTTCTAATGCAT  540

541 TGGACCAGAGAAATTTAAAACTCAAATGAACTGTAAAGTTTCCACACTGACACTGTTGGG  600

601 CTAATAGTATTCCCATGTGCAAGGCATGCATCTTTTCTTCCCCAGAGCAATGCCTCTCAT  660

661 GAGAGAGCTAATGGTATTGCAATCAGCTGCTGATTGTTTTCTCTGTTCCCATTTTCTGGG  720

721 TGAAGGAAGAAAGAGCAAAAAAGTGTGTGCTTGTGAGAGAGGAGGGATGGTAGATAGGCA  780

781 GAGGCAGGCTCAGAATGGAAGGACCACGTATCTTGGAATATTACTAAGTCAGGACTTGAG  840

841 TGAAAAAAGACTAAAGGTAAGCAAATTATAAAAGGATTTAGGAAACGCAGTCCGGTATTG  900

901 GATATTGCTTAAAGAAAATTCCCTTATAAGTTTATACTTCCAAGACTCTGAATTGGATTA  960

961 CTGCAAACATCATTAAGTGTTTCTAATTTAATCCCATGAGAGTAATGGAATCCTTGCTCT 1020
```

Figure 1B
Heregulin-like Factor

```
1021  GAGACATGCACTCTTACTTTTTCAGGATGATTTACCAGACTAGAACCTCCTGATTTCCCC  1080

1081  TTTTTTGTGTGTGTGAATGAACCCCTGATAAAATCTTGTGGCTGTAACATGCTCCTTAAA  1140

1141  ATGCTGATATGATAGATTTATTTTTAACAATAGGCTATAGATTAGCTGTTAGGAAGCAAA  1200

1201  TAGATTATTACAACAGGATTAAAGCAACTAAGAGTGCTAGAGATAAAAGTCTCCCAAATA  1260

1261  ATTGGAAAGATAAAAGAAATATCTTAAAAAACAGAGCTACATCACACTGATATTGTAAAT  1320

1321  TCAAAATGGGTAATGAAGCTCAAAGCCTCCAAAGCTTGCAGCAAGTGCTGGTGAATTGCT  1380

1381  TGGGAAGATGCAACTAGTGTAATCTTTTACCTTTGGGTCAATGTTCTGATTCTTTTGCAG  1440

1441  CTTCTGCTCACAAGACTGAGCTTGCTTGATGGTATCGGGAAAGATATGAACATTTTGCGT  1500

1501  GTGCCTCCACATGCAGCCACCACAGTGTCCGTGGAAGATAGCTTTTATGAACTTCATTTA  1560

1561  CAGAGGAGGAAATGGAGGCTCAACAAGTTTAGGAAATTATTAGGGTAGCAAAACTAGTGG  1620

1621  GTAGCAGAGTGGGATTCAAATCCCAGTCCCTGTGATACAATAAGCCACGCTCTGTAGGGT  1680

1681  GCTACTGACTGGAGAAGCTCATTGCTAAGACCGGCCATGTGCTCCACTGACGGCACTATC  1740

1741  TTTGTCAGAGACGTTGGAAGACAGGCAAAATTCAAGGGCATGATTCTACTGGGAAAGTTG  1800

1801  TCAGAATCAAAATGGAGTCATTTGTGTTAAAAACCCTGACAAATAGAGCCGGAGAAGGAC  1860

1861  ATGAAGGGAGCAGTCACGTAGGCAAATGCCTGATTACAAGAACTATCACAAAAGTCTGTG  1920

1921  AAAACCGCAGCTTTGCATGAAGACTATTGCAGCCTTACACGCACGAAAATAGTTCTGCAA  1980

1981  GGACATATGCCCAGCAACTTCCTGTCCACCCTTGGACTGGCTCCTCCTTTCTTGGGATCC  2040

2041  TTGCAGCCAAGGATAGTGACCTCAAATCAGTTGTGTACCTAACGTTTCCTGTCTTCCTAG  2100

2101  TGATAAAACATAGTTTCCTATATCGTGTGTATTCCCATTGCAACACTTATTTCCAAATAA  2160

2161  ATATTTTCTTTTAGAGTCTCAAAAAAAAAAAAAAAAAAA  2199
```

Figure 2

Heregulin-like Factor
x
Human Heregulin

Percent Similarity: 55.782   Percent Identity: 32.653

```
  2 SSSSATTTTPETSTSPKFHTTTYSTERSEHFKPCRDKDLAYCLNDGECFV  51
    || |        |       | ||    |   |   | | ||||
149 SSESPIRISVSTEGANTSSSTSTSTTGTSHLVKCAEKEKTFCVNGGECFM 198

52 IETLTGSHKH.CRCKEGYQGVRCDQFLPKTDSILSDPNHLGIEFMESEEV 100
    |         ||   | ||            |   ||||||| ||
199 VKDLSNPSRYLCKCPNEFTGDRCQNYV.....MASFYKHLGIEFMEAEEL 243

101 YQRQVLSISCIIFGIVIVGMFCAAFYFKSKRNITANSVSEERWKGLPSQE 150
    || || |  |     ||  |  | |  |                  | |
244 YQKRVLTITGICIALLVVGIMCVVAYCKTKKQ..RKKLHDRLRQSLRSER 291

151 PNLQQ 155
      |
292 NNMMN 296
```

Heregulin-like Factor

Figure 5

Amino Acid Sequences of EGF Binding Domains

```
                      6         14    20              31              42
αTGF       SHFNDCPDSHTQFCFHG-TCRFLVQEDKP---ACVCHSGYVGARCEHADLLA
EGF        RNSDSECPLSHDGYCLHDGVCMYIEALDKY---ACNCVVGYIGERCOYRDLKW
HB-EGF     GKKRDPCLRKYKDFCIHG-ECKYVKELRAP---SCICHPGYGGERCHGLSLP
Amph       RKKKNPCNAEFQNFCIHG-ECKYIEHLEAV---TCKCQQEYFGERCGEKSMKT
βcell      KGHFSRCPKQYKHYCIKG-RCRFVVAEQTP---SCVCDEGYIGARCERVDLFY
neuR       TSHLIKCAEKEKTFCVNGGECFTVKDLSNPSRYLCKCOPGFTGARCTENVPMK
Hrgα1      TSHLVKCAEKEKTFCVNGGECFMVKDLSNPSRYLCKCQPGFTGARCTENVPMK
Hrgβ1      TSHLVKCAEKEKTFCVNGGECFMVKDLSNPSRYLCKCPNEFTGDRCQNYVMAS
HRG-2      SGHARKCNETAKSYCVNGGVCYYIEGINQLS---CKCPVGYTGDRCQQFAMVN
HLF        SEHFKPCRDKDLAYCLNDGECFVIETLTGSHK-HCRCKEGYQGVRCDQFLPKT
```

SEQUENCE LISTING

<160> NUMBER OF SEQ ID NOS: 22

<210> SEQ ID NO 1
<211> LENGTH: 2199
<212> TYPE: DNA
<213> ORGANISM: Homo sapiens

<400> SEQUENCE: 1

```
ctcttcttcc tcctccgcta ccaccaccac accagaaact agcaccagcc ccaaatttca      60
tacgacgaca tattccacag agcgatccga gcacttcaaa ccctgccgag acaaggacct     120
tgcatactgt ctcaatgatg gcgagtgctt tgtgatcgaa accctgaccg gatcccataa     180
acactgtcgg tgcaaagaag gctaccaagg agtccgttgt gatcaatttc tgccgaaaac     240
tgattccatc ttatcggatc caaccactt ggggattgaa ttcatggaga gtgaagaagt     300
ttatcaaagg caggtgctgt caatttcatg tatcatcttt ggaattgtca tcgtgggcat     360
gttctgtgca gcattctact tcaaaagcaa aaggaatatt acagcaaatt ctgtgtctga     420
ggaaagatgg aagggtctgc cttcccagga gcccaatctg caacaagaca ataatgcct      480
aacaatggat taatgatgtc tactattctg caacttacat ctcatttctt tctaatgcat     540
tggaccagag aaatttaaaa ctcaaatgaa ctgtaaagtt tccacactga cactgttggg     600
ctaatagtat tcccatgtgc aaggcatgca tcttttcttc cccagagcaa tgcctctcat     660
gagagagcta atggtattgc aatcagctgc tgattgtttt ctctgttccc attttctggg     720
tgaaggaaga aagagcaaaa aagtgtgtgc ttgtgagaga ggagggatgg tagataggca     780
gaggcaggct cagaatggaa ggaccacgta tcttggaata ttactaagtc aggacttgag     840
tgaaaaaaga ctaaaggtaa gcaaattata aaaggattta ggaaacgcag tccggtattg     900
gatattgctt aaagaaaatt cccttataag tttatacttc caagactctg aattggatta     960
ctgcaaacat cattaagtgt ttctaattta atcccatgag agtaatggaa tccttgctct    1020
gagacatgca ctcttacttt ttcaggatga tttaccagac tagaacctcc tgatttcccc    1080
tttttttgtgt gtgtgaatga acccctgata aaatcttgtg gctgtaacat gctccttaaa    1140
atgctgatat gatagattta tttttaacaa taggctatag attagctgtt aggaagcaaa    1200
tagattatta caacaggatt aaagcaacta agagtgctag agataaaagt ctcccaaata    1260
attggaaaga taaagaaat atcttaaaaa acagagctac atcacactga tattgtaaat    1320
tcaaaatggg taatgaagct caaagcctcc aaagcttgca gcaagtgctg gtgaattgct    1380
tgggaagatg caactagtgt aatcttttac ctttgggtca atgttctgat tcttttgcag    1440
cttctgctca caagactgag cttgcttgat ggtatcggga aagatatgaa cattttgcgt    1500
gtgcctccac atgcagccac cacagtgtcc gtggaagata gcttttatga acttcattta    1560
cagaggagga aatggaggct caacaagttt aggaaattat tagggtagca aaactagtgg    1620
gtagcagagt gggattcaaa tcccagtccc tgtgatacaa taagccacgc tctgtagggt    1680
gctactgact ggagaagctc attgctaaga ccggccatgt gctccactga cggcactatc    1740
tttgtcagag acgttggaag acaggcaaaa ttcaagggca tgattctact gggaaagttg    1800
tcagaatcaa aatggagtca tttgtgttaa aaaccctgac aaatagagcc ggagaaggac    1860
```

```
atgaaggagg cagtcacgta ggcaaatgcc tgattacaag aactatcaca aaagtctgtg    1920
aaaaccgcag ctttgcatga agactattgc agccttacac gcacgaaaat agttctgcaa    1980
ggacatatgc ccagcaactt cctgtccacc cttggactgg ctcctccttt cttgggatcc    2040
ttgcagccaa ggatagtgac ctcaaatcag ttgtgtacct aacgtttcct gtcttcctag    2100
tgataaaaca tagtttccta tatcgtgtgt attcccattg caacacttat ttccaaataa    2160
atattttctt ttagagtctc aaaaaaaaaa aaaaaaaa                            2199
```

<210> SEQ ID NO 2
<211> LENGTH: 157
<212> TYPE: PRT
<213> ORGANISM: Homo sapiens

<400> SEQUENCE: 2

```
Ser Ser Ser Ser Ala Thr Thr Thr Pro Glu Thr Ser Thr Ser
 1               5                  10                  15

Pro Lys Phe His Thr Thr Thr Tyr Ser Thr Glu Arg Ser Glu His Phe
             20                  25                  30

Lys Pro Cys Arg Asp Lys Asp Leu Ala Tyr Cys Leu Asn Asp Gly Glu
         35                  40                  45

Cys Phe Val Ile Glu Thr Leu Thr Gly Ser His Lys His Cys Arg Cys
     50                  55                  60

Lys Glu Gly Tyr Gln Gly Val Arg Cys Asp Gln Phe Leu Pro Lys Thr
 65                  70                  75                  80

Asp Ser Ile Leu Ser Asp Pro Asn His Leu Gly Ile Glu Phe Met Glu
                 85                  90                  95

Ser Glu Glu Val Tyr Gln Arg Gln Val Leu Ser Ile Ser Cys Ile Ile
            100                 105                 110

Phe Gly Ile Val Ile Val Gly Met Phe Cys Ala Ala Phe Tyr Phe Lys
        115                 120                 125

Ser Lys Arg Asn Ile Thr Ala Asn Ser Val Ser Glu Glu Arg Trp Lys
    130                 135                 140

Gly Leu Pro Ser Gln Glu Pro Asn Leu Gln Gln Asp Lys
145                 150                 155
```

<210> SEQ ID NO 3
<211> LENGTH: 645
<212> TYPE: PRT
<213> ORGANISM: Homo sapiens

<400> SEQUENCE: 3

```
Met Ser Glu Arg Lys Glu Gly Arg Gly Lys Gly Lys Gly Lys Lys Lys
 1               5                  10                  15

Glu Arg Gly Ser Gly Lys Lys Pro Glu Ser Ala Ala Gly Ser Gln Ser
             20                  25                  30

Pro Ala Leu Pro Pro Gln Leu Lys Glu Met Lys Ser Gln Glu Ser Ala
         35                  40                  45

Ala Gly Ser Lys Leu Val Leu Arg Cys Glu Thr Ser Ser Glu Tyr Ser
     50                  55                  60

Ser Leu Arg Phe Lys Trp Phe Lys Asn Gly Asn Glu Leu Asn Arg Lys
 65                  70                  75                  80

Asn Lys Pro Gln Asn Ile Lys Ile Gln Lys Lys Pro Gly Lys Ser Glu
                 85                  90                  95

Leu Arg Ile Asn Lys Ala Ser Leu Ala Asp Ser Gly Glu Tyr Met Cys
            100                 105                 110
```

```
Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
        130                 135                 140

Gly Ala Tyr Val Ser Ser Glu Ser Pro Ile Arg Ile Ser Val Ser Thr
145                 150                 155                 160

Glu Gly Ala Asn Thr Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
        210                 215                 220

Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
            245                 250                 255

Ala Leu Leu Val Val Gly Ile Met Cys Val Val Ala Tyr Cys Lys Thr
        260                 265                 270

Lys Lys Gln Arg Lys Lys Leu His Asp Arg Leu Arg Gln Ser Leu Arg
        275                 280                 285

Ser Glu Arg Asn Asn Met Met Asn Ile Ala Asn Gly Pro His His Pro
    290                 295                 300

Asn Pro Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
            340                 345                 350

Thr Gln Thr Pro Ser His Ser Trp Ser Asn Gly His Thr Glu Ser Ile
        355                 360                 365

Leu Ser Glu Ser His Ser Val Ile Val Met Ser Ser Val Glu Asn Ser
    370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
            420                 425                 430

Met Thr Thr Pro Ala Arg Met Ser Pro Val Asp Phe His Thr Pro Ser
        435                 440                 445

Ser Pro Lys Ser Pro Ser Glu Met Ser Pro Val Ser Ser Met
    450                 455                 460         Met

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His Asn Pro Ala His
            500                 505                 510

Asp Ser Asn Ser Leu Pro Ala Ser Pro Leu Arg Ile Val Glu Asp Glu
        515                 520                 525
```

```
Glu Tyr Glu Thr Thr Gln Glu Tyr Glu Pro Ala Gln Glu Pro Val Lys
    530                 535                 540
Lys Leu Ala Asn Ser Arg Arg Ala Lys Arg Thr Lys Pro Asn Gly His
545                 550                 555                 560
Ile Ala Asn Arg Leu Glu Val Asp Ser Asn Thr Ser Ser Gln Ser Ser
                565                 570                 575
Asn Ser Glu Ser Glu Thr Glu Asp Glu Arg Val Gly Glu Asp Thr Pro
            580                 585                 590
Phe Leu Gly Ile Gln Asn Pro Leu Ala Ala Ser Leu Glu Ala Thr Pro
        595                 600                 605
Ala Phe Arg Leu Ala Asp Ser Arg Thr Asn Pro Ala Gly Arg Phe Ser
    610                 615                 620
Thr Gln Glu Glu Ile Gln Ala Arg Leu Ser Ser Val Ile Ala Asn Gln
625                 630                 635                 640
Asp Pro Ile Ala Val
                645

<210> SEQ ID NO 4
<211> LENGTH: 536
<212> TYPE: DNA
<213> ORGANISM: Homo sapiens
<220> FEATURE:
<221> NAME/KEY: misc_feature
<222> LOCATION: (315)
<223> OTHER INFORMATION: n equals a,t,g, or c
<220> FEATURE:
<221> NAME/KEY: misc_feature
<222> LOCATION: (316)
<223> OTHER INFORMATION: n equals a,t,g, or c
<220> FEATURE:
<221> NAME/KEY: misc_feature
<222> LOCATION: (331)
<223> OTHER INFORMATION: n equals a,t,g, or c
<220> FEATURE:
<221> NAME/KEY: misc_feature
<222> LOCATION: (335)
<223> OTHER INFORMATION: n equals a,t,g, or c
<220> FEATURE:
<221> NAME/KEY: misc_feature
<222> LOCATION: (349)
<223> OTHER INFORMATION: n equals a,t,g, or c
<220> FEATURE:
<221> NAME/KEY: misc_feature
<222> LOCATION: (350)
<223> OTHER INFORMATION: n equals a,t,g, or c
<220> FEATURE:
<221> NAME/KEY: misc_feature
<222> LOCATION: (368)
<223> OTHER INFORMATION: n equals a,t,g, or c
<220> FEATURE:
<221> NAME/KEY: misc_feature
<222> LOCATION: (370)
<223> OTHER INFORMATION: n equals a,t,g, or c
<220> FEATURE:
<221> NAME/KEY: misc_feature
<222> LOCATION: (381)
<223> OTHER INFORMATION: n equals a,t,g, or c
<220> FEATURE:
<221> NAME/KEY: misc_feature
<222> LOCATION: (387)
<223> OTHER INFORMATION: n equals a,t,g, or c
<220> FEATURE:
<221> NAME/KEY: misc_feature
<222> LOCATION: (388)
<223> OTHER INFORMATION: n equals a,t,g, or c
<220> FEATURE:
<221> NAME/KEY: misc_feature
<222> LOCATION: (403)
<223> OTHER INFORMATION: n equals a,t,g, or c
<220> FEATURE:
<221> NAME/KEY: misc_feature
```

<222> LOCATION: (409)
<223> OTHER INFORMATION: n equals a,t,g, or c
<220> FEATURE:
<221> NAME/KEY: misc_feature
<222> LOCATION: (434)
<223> OTHER INFORMATION: n equals a,t,g, or c
<220> FEATURE:
<221> NAME/KEY: misc_feature
<222> LOCATION: (452)
<223> OTHER INFORMATION: n equals a,t,g, or c
<220> FEATURE:
<221> NAME/KEY: misc_feature
<222> LOCATION: (504)
<223> OTHER INFORMATION: n equals a,t,g, or c
<220> FEATURE:
<221> NAME/KEY: misc_feature
<222> LOCATION: (507)
<223> OTHER INFORMATION: n equals a,t,g, or c
<220> FEATURE:
<221> NAME/KEY: misc_feature
<222> LOCATION: (521)
<223> OTHER INFORMATION: n equals a,t,g, or c
<220> FEATURE:
<221> NAME/KEY: misc_feature
<222> LOCATION: (527)
<223> OTHER INFORMATION: n equals a,t,g, or c

<400> SEQUENCE: 4
ggcacagctc ttcttcctcc tccgctacca ccaccacacc agaaactagc accagcccca      60
aatttcatac gacgacatat tccacagagc gatccgagca cttcaaaccc tgccgagaca     120
aggaccttgg catactgtct caatgatggc gagtgctttg tgatcgaaac cctgaccgga     180
tcccattaaa cactgtcggt gcaaagaagg ctaccaagga gtccgttgtg atcaatttct     240
gccgaaaact gattccatct tatcggatcc aaaccacttg gggattggaa ttcatgggag     300
agtgaagaag ttttnnccaa agggcaggtg ntgtncaatt tccaagtgnn caactttggg     360
gattggtncn tcgtgggggc ntgtttnngg tggcagcatt tcntaactnc caaaaagcca     420
aaaagggatt tttnaccggc aaatttccgt gntctgaagg gaaaattggg aagggtcttg     480 cccttttcccc aggaggccca attnggncaa caaggccaat natggcntaa caaggg       536

<210> SEQ ID NO 5
<211> LENGTH: 25
<212> TYPE: DNA
<213> ORGANISM: Artificial sequence
<220> FEATURE:
<223> OTHER INFORMATION: 5' primer for cloning the EGF like domain of
      the HLF protein

<400> SEQUENCE: 5
ggcggatccc tcttcttcct cctcc                                            25

<210> SEQ ID NO 6
<211> LENGTH: 42
<212> TYPE: DNA
<213> ORGANISM: Artificial sequence
<220> FEATURE:
<223> OTHER INFORMATION: 3' primer for cloning the EGF like domain of
      the HLF protein

<400> SEQUENCE: 6
ggcgaattct aaacttcttc actctccatg aattcaatcc cc                          42

<210> SEQ ID NO 7
<211> LENGTH: 26
<212> TYPE: DNA
<213> ORGANISM: Artificial sequence
<220> FEATURE:

```
<223> OTHER INFORMATION: 5' primer for amplifying the mature HLF
      sequence

<400> SEQUENCE: 7
ggcggatccc ctcttcttcc tcctcc                                            26

<210> SEQ ID NO 8
<211> LENGTH: 42
<212> TYPE: DNA
<213> ORGANISM: Artificial sequence
<220> FEATURE:
<223> OTHER INFORMATION: 3' primer for amplifying the mature HLF
      sequence

<400> SEQUENCE: 8
ggcggtacct aaacttcttc actctccatg aattcaatcc cc                          42

<210> SEQ ID NO 9
<211> LENGTH: 120
<212> TYPE: DNA
<213> ORGANISM: Artificial sequence
<220> FEATURE:
<223> OTHER INFORMATION: 5' primer, containing a Bam HI site, a Kozak
      sequence, an AUG start codon, a sequence encoding the secretory
      leader peptide from the human IL-6 gene, and 16 nucleotides of the
      5' coding region of the extracellular domain of the HLF
      polypeptide

<400> SEQUENCE: 9
gccggatccg ccaccatgaa ctccttctcc acaagcgcct tcggtccagt tgccttctcc       60
ctggggctgc tcctggtgtt gcctgctgcc ttccctgccc cagtctcttc ttcctcctcc      120

<210> SEQ ID NO 10
<211> LENGTH: 42
<212> TYPE: DNA
<213> ORGANISM: Artificial sequence
<220> FEATURE:
<223> OTHER INFORMATION: 3' primer, containing the Xba I and 33
      nucleotides complementary to the 3' coding sequence OF HLF
      immediately before the stop codon

<400> SEQUENCE: 10
ggctctagat aaacttcttc actctccatg aattcaatcc cc                          42

<210> SEQ ID NO 11
<211> LENGTH: 48
<212> TYPE: PRT
<213> ORGANISM: Homo sapiens

<400> SEQUENCE: 11
```

Ser His Phe Asn Asp Cys Pro Asp Ser His Thr Gln Phe Cys Phe His
 1               5                  10                  15

Gly Thr Cys Arg Phe Leu Val Gln Glu Asp Lys Pro Ala Cys Val Cys
            20                  25                  30

His Ser Gly Tyr Val Gly Ala Arg Cys Glu His Ala Asp Leu Leu Ala
        35                  40                  45

```
<210> SEQ ID NO 12
<211> LENGTH: 50
<212> TYPE: PRT
<213> ORGANISM: Homo sapiens

<400> SEQUENCE: 12
```

Arg Asn Ser Asp Ser Glu Cys Pro Leu Ser His Asp Gly Tyr Cys Leu
 1               5                  10                  15

-continued

His Asp Gly Val Cys Met Tyr Ile Glu Ala Leu Asp Lys Tyr Ala Cys
              20                  25                  30

Asn Cys Val Val Gly Tyr Ile Gly Glu Arg Cys Gln Tyr Arg Asp Leu
              35                  40                  45

Lys Trp
    50

<210> SEQ ID NO 13
<211> LENGTH: 48
<212> TYPE: PRT
<213> ORGANISM: Homo sapiens

<400> SEQUENCE: 13

Gly Lys Lys Arg Asp Pro Cys Leu Arg Lys Tyr Lys Asp Phe Cys Ile
  1               5                  10                  15

His Gly Glu Cys Lys Tyr Val Lys Glu Leu Arg Ala Pro Ser Cys Ile
              20                  25                  30

Cys His Pro Gly Tyr Gly Gly Glu Arg Cys His Gly Leu Ser Leu Pro
              35                  40                  45

<210> SEQ ID NO 14
<211> LENGTH: 49
<212> TYPE: PRT
<213> ORGANISM: Homo sapiens

<400> SEQUENCE: 14

Arg Lys Lys Lys Asn Pro Cys Asn Ala Glu Phe Gln Asn Phe Cys Ile
  1               5                  10                  15

His Gly Glu Cys Lys Tyr Ile Glu His Leu Glu Ala Val Thr Cys Lys
              20                  25                  30

Cys Gln Gln Glu Tyr Phe Gly Glu Arg Cys Gly Glu Lys Ser Met Lys
              35                  40                  45

Thr

<210> SEQ ID NO 15
<211> LENGTH: 49
<212> TYPE: PRT
<213> ORGANISM: Homo sapiens

<400> SEQUENCE: 15

Lys Gly His Phe Ser Arg Cys Pro Lys Gln Tyr Lys His Tyr Cys Ile
  1               5                  10                  15

Lys Gly Arg Cys Arg Phe Val Val Ala Glu Gln Thr Pro Ser Cys Val
              20                  25                  30

Cys Asp Glu Gly Tyr Ile Gly Ala Arg Cys Glu Arg Val Asp Leu Phe
              35                  40                  45

Tyr

<210> SEQ ID NO 16
<211> LENGTH: 52
<212> TYPE: PRT
<213> ORGANISM: Homo sapiens

<400> SEQUENCE: 16

Thr Ser His Leu Ile Lys Cys Ala Glu Lys Glu Lys Thr Phe Cys Val
  1               5                  10                  15

Asn Gly Gly Glu Cys Phe Thr Val Lys Asp Leu Ser Asn Pro Ser Arg
              20                  25                  30

```
Tyr Leu Cys Lys Cys Pro Gly Phe Thr Gly Ala Arg Cys Thr Glu Asn
        35                  40                  45

Val Pro Met Lys
    50

<210> SEQ ID NO 17
<211> LENGTH: 53
<212> TYPE: PRT
<213> ORGANISM: Homo sapiens

<400> SEQUENCE: 17

Thr Ser His Leu Val Lys Cys Ala Glu Lys Glu Lys Thr Phe Cys Val
 1               5                  10                  15

Asn Gly Gly Glu Cys Phe Met Val Lys Asp Leu Ser Asn Pro Ser Arg
                20                  25                  30

Tyr Leu Cys Lys Cys Gln Pro Gly Phe Thr Gly Ala Arg Cys Thr Glu
        35                  40                  45

Asn Val Pro Met Lys
    50

<210> SEQ ID NO 18
<211> LENGTH: 53
<212> TYPE: PRT
<213> ORGANISM: Homo sapiens

<400> SEQUENCE: 18

Thr Ser His Leu Val Lys Cys Ala Glu Lys Glu Lys Thr Phe Cys Val
 1               5                  10                  15

Asn Gly Gly Glu Cys Phe Met Val Lys Asp Leu Ser Asn Pro Ser Arg
                20                  25                  30

Tyr Leu Cys Lys Cys Pro Asn Glu Phe Thr Gly Asp Arg Cys Gln Asn
        35                  40                  45

Tyr Val Met Ala Ser
    50

<210> SEQ ID NO 19
<211> LENGTH: 50
<212> TYPE: PRT
<213> ORGANISM: Homo sapiens

<400> SEQUENCE: 19

Ser Gly His Ala Arg Lys Cys Asn Glu Thr Ala Lys Ser Tyr Cys Val
 1               5                  10                  15

Asn Gly Gly Val Cys Tyr Tyr Ile Glu Gly Ile Asn Gln Leu Ser Cys
                20                  25                  30

Lys Cys Pro Val Gly Tyr Thr Gly Asp Arg Cys Gln Gln Phe Ala Met
        35                  40                  45

Val Asn
    50

<210> SEQ ID NO 20
<211> LENGTH: 20
<212> TYPE: DNA
<213> ORGANISM: Artificial sequence
<220> FEATURE:
<223> OTHER INFORMATION: downstream primer for synthesizing HLF cDNA

<400> SEQUENCE: 20
ccacgatgac aattccaaag                                              20
```

-continued

```
<210> SEQ ID NO 21
<211> LENGTH: 20
<212> TYPE: DNA
<213> ORGANISM: Artificial sequence
<220> FEATURE:
<223> OTHER INFORMATION: upstream primer for HLF PCR

<400> SEQUENCE: 21
taccaccacc acaccagaaa                                                   20

<210> SEQ ID NO 22
<211> LENGTH: 720
<212> TYPE: PRT
<213> ORGANISM: Homo sapiens

<400> SEQUENCE: 22
```

Met Ser Glu Gly Ala Ala Ala Ser Pro Gly Ala Ala Ser Ala
 1               5                  10                  15

Ala Ala Ala Ser Ala Glu Glu Gly Thr Ala Ala Ala Ala Ala
                20                  25                  30

Ala Ala Gly Gly Gly Pro Asp Gly Gly Glu Gly Ala Ala Glu Pro
            35                  40                  45

Pro Arg Glu Leu Arg Cys Ser Asp Cys Ile Val Trp Asn Arg Gln
 50                  55                  60

Thr Trp Leu Cys Val Val Pro Leu Phe Ile Gly Phe Ile Gly Leu Gly
 65                  70                  75                  80

Leu Ser Leu Met Leu Leu Lys Trp Ile Val Val Gly Ser Val Lys Glu
                85                  90                  95

Tyr Val Pro Thr Asp Leu Val Asp Ser Lys Gly Met Gly Gln Asp Pro
                100                 105                 110

Phe Phe Leu Ser Lys Pro Ser Ser Phe Pro Lys Ala Met Glu Thr Thr
            115                 120                 125

Thr Thr Thr Thr Ser Thr Thr Ser Pro Ala Thr Pro Ser Ala Gly Gly
130                 135                 140

Ala Ala Ser Ser Arg Thr Pro Asn Arg Ile Ser Thr Arg Leu Thr Thr
145                 150                 155                 160

Ile Thr Arg Ala Pro Thr Arg Phe Pro Gly His Arg Val Pro Ile Arg
                165                 170                 175

Ala Ser Pro Arg Ser Thr Thr Ala Arg Asn Thr Ala Ala Pro Ala Thr
            180                 185                 190

Val Pro Ser Thr Thr Ala Pro Phe Phe Ser Ser Ser Thr Leu Gly Ser
            195                 200                 205

Arg Pro Pro Val Pro Gly Thr Pro Ser Thr Gln Ala Met Pro Ser Trp
210                 215                 220

Pro Thr Ala Ala Tyr Ala Thr Ser Ser Tyr Leu His Asp Ser Thr Pro
225                 230                 235                 240

Ser Trp Thr Leu Ser Pro Phe Gln Asp Ala Ala Ser Ser Ser Ser
                245                 250                 255

Ser Ser Ser Ser Ser Thr Thr Thr Pro Glu Thr Ser Thr Ser Pro
            260                 265                 270

Lys Phe His Thr Thr Thr Tyr Ser Thr Glu Arg Ser Glu His Phe Lys
            275                 280                 285

Pro Cys Arg Asp Lys Asp Leu Ala Tyr Cys Leu Asn Asp Gly Glu Cys
            290                 295                 300

Phe Val Ile Glu Thr Leu Thr Gly Ser His Lys His Cys Arg Cys Lys
305                 310                 315                 320

-continued

```
Glu Gly Tyr Gln Gly Val Arg Cys Asp Gln Phe Leu Pro Lys Thr Asp
            325                 330                 335

Ser Ile Leu Ser Asp Pro Thr Asp His Leu Gly Ile Glu Phe Met Glu
            340                 345                 350

Ser Glu Glu Val Tyr Gln Arg Gln Val Leu Ser Ile Ser Cys Ile Ile
            355                 360                 365

Phe Gly Ile Val Ile Val Gly Met Phe Cys Ala Ala Phe Tyr Phe Lys
            370                 375                 380

Ser Lys Lys Gln Ala Lys Gln Ile Gln Glu Gln Leu Lys Val Pro Gln
385                 390                 395                 400

Asn Gly Lys Ser Tyr Ser Leu Lys Ala Ser Ser Thr Met Ala Lys Ser
            405                 410                 415

Glu Asn Leu Val Lys Ser His Val Gln Leu Gln Asn Tyr Ser Lys Val
            420                 425                 430

Glu Arg His Pro Val Thr Ala Leu Glu Lys Met Met Glu Ser Ser Phe
            435                 440                 445

Val Gly Pro Gln Ser Phe Pro Glu Val Pro Ser Pro Asp Arg Gly Ser
            450                 455                 460

Gln Ser Val Lys His His Arg Ser Leu Ser Ser Cys Cys Ser Pro Gly
465                 470                 475                 480

Gln Arg Ser Gly Met Leu His Arg Asn Ala Phe Arg Arg Thr Pro Pro
            485                 490                 495

Ser Pro Arg Ser Arg Leu Gly Gly Ile Val Gly Pro Ala Tyr Gln Gln
            500                 505                 510

Leu Glu Glu Ser Arg Ile Pro Asp Gln Asp Thr Ile Pro Cys Gln Gly
            515                 520                 525

Ile Glu Val Arg Lys Thr Ile Ser His Leu Pro Ile Gln Leu Trp Cys
            530                 535                 540

Val Glu Arg Pro Leu Asp Leu Lys Tyr Ser Ser Gly Leu Lys Thr
545                 550                 555                 560

Gln Arg Asn Thr Ser Ile Asn Met Gln Leu Pro Ser Arg Glu Thr Asn
            565                 570                 575

Pro Tyr Phe Asn Ser Leu Glu Gln Lys Asp Leu Val Gly Tyr Ser Ser
            580                 585                 590

Thr Arg Ala Ser Ser Val Pro Ile Ile Pro Ser Val Gly Leu Glu Glu
            595                 600                 605

Thr Cys Leu Gln Met Pro Gly Ile Ser Glu Val Lys Ser Ile Lys Trp
            610                 615                 620

Cys Lys Asn Ser Tyr Ser Ala Asp Val Val Asn Val Ser Ile Pro Val
625                 630                 635                 640

Ser Asp Cys Leu Ile Ala Glu Gln Gln Glu Val Lys Ile Leu Leu Glu
            645                 650                 655

Thr Val Gln Glu Gln Ile Arg Ile Leu Thr Asp Ala Arg Arg Ser Glu
            660                 665                 670

Asp Tyr Glu Leu Ala Ser Val Glu Thr Glu Asp Ser Ala Ser Glu Asn
            675                 680                 685

Thr Ala Phe Leu Pro Leu Ser Pro Thr Ala Lys Ser Glu Arg Glu Ala
            690                 695                 700

Gln Phe Val Leu Arg Asn Glu Ile Gln Arg Asp Ser Ala Leu Thr Lys
705                 710                 715                 720
```

US 7,049,409 B2

HEREGULIN-LIKE FACTOR ANTIBODIES

CROSS REFERENCE TO RELATED APPLICATIONS

This application is a divisional of U.S. application Ser. No. 09/097,681, filed Jun. 16, 1998, now U.S. Pat. No. 6,727,077, which claims benefit under 35 U.S.C. § 119(e) of U.S. Provisional Application No. 60/049,942, filed on Jun. 17, 1997, which is herein incorporated by reference in its entirety.

FIELD OF THE INVENTION

The present invention relates to a novel human gene encoding a polypeptide which is a novel member of the heregulin family. More specifically, isolated nucleic acid molecules are provided encoding a human polypeptide named heregulin-like factor, hereinafter referred to as "HLF". HLF polypeptides are also provided, as are vectors, host cells and recombinant methods for producing the same. Also provided are diagnostic methods for detecting disorders related to primary cancers, and therapeutic methods for treating such disorders. The invention further relates to screening methods for identifying agonists and antagonists of HLF activity.

BACKGROUND OF THE INVENTION

The proto-oncogene termed erbB2 (or HER2) encodes a 185 kDa transmembrane tyrosine kinase molecule designated p185erbB2. The overexpression of this receptor molecule correlates strongly with a poor prognosis in a number of human cancers including, among others, breast, ovarian, endometrium, fallopian tube, cervix, and colon (Nowak, F., et al., *Exp. Cell Res.* 231:251–259; 1997; Cirisano, F. D. and Karlan, B. Y., *J. Soc. Gynecol. Investig.* 3(3):99–105; 1996). Variously spliced transcripts of the heregulin (HRG) gene have been found to indirectly stimulate p185erbB2 through transphosphorylation or receptor heterodimerization with erbB3 and p180erbB4. A 45 kDa protein, designated HRG-alpha, specifically induces tyrosine phosphorylation of p185erbB2 and has been purified from the conditioned medium of a human breast tumor cell line (Holmes, W. E., et al., *Science* 256:1205–1210; 1992). A second, related HRG molecule of 52 kDa, which may be the product of a novel gene, rather than a novel HRG gene splice product, has been identified which exhibits similar characteristics including induction of transient membrane ruffling, lamellipodia formation, cell motility and proliferation of human breast cancer cells (Kung, W., et al., *Biochem. Biophys. Res. Commun.* 202(3):1357–1365; 1994). In addition, more recent studies have reported that heregulins can induce tyrosine phosphorylation not only of p185erbB2, but of several additional EGFR-related family members including erbB3 and p180erbB4 (Tzahar, E., et al., *J. Biol. Chem.* 269:25226–25223; 1994; Plowman, G. D., et al., *Nature* 366:473–475; 1993).

Lewis and colleagues (*Cancer Res.* 56:1457–1465; 1996) recently performed an extensive analysis of the effects of the heregulin family of proteins on a panel of breast and ovarian tumor cell lines. The biological responses to HRG were also compared to EGF and to the growth-inhibitory anti-ErbB2 antibody 4D5. In nearly all cases, HRG stimulation of DNA synthesis correlated with positive effects on cell cycle progression and cell number and with enhancement of colony formation in soft agar. In addition to the effects of the heregulin family of proteins on breast and ovarian cells, similar effects have also been recently observed on human Schwann cells (Levi, A. D., et al., *J. Neurosci.* 15(2):1329–1340; 1995; Morrissey, T. K., et al., *Proc. Natl. Acad. Sci. USA* 92(5):1431–1435; 1995) suggesting that the heregulin family of proteins play a key role in the genesis of a number of cancers.

The heregulin family of proteins consists at least of a number of splice variants of heregulin, the Neu differentiating factor, the glial growth factors-I, -II, and -III, and a protein that stimulates muscle acetylcholine receptor synthesis (ARIA). In addition to the obvious role such polypeptides may play in oncogenic events, these proteins have also been exploited as Pseudomonas exotoxin A fusion proteins to inhibit the growth of several mammary carcinoma cell lines as well as to cause growth retardation of transplanted human breast tumor cells in mice (Jeschke, M., et al., *Int. J. Cancer* 60(5):730–739;1995).

Thus, there is a need for polypeptides that function as regulators of oncogenic events and existing tumors. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the HLF polypeptide having the complete amino acid sequence shown in SEQ ID NO:2 or the complete amino acid sequence encoded by the cDNA clone was deposited as DNA plasmid with the American Type Culture Collection ("ATCC") on Jun. 19, 1997, and assigned ATCC Deposit Number 209123. The ATCC is located at 10801 University Boulevard, Manassas, Va. 20110-2209. The nucleotide sequence determined by sequencing the deposited HLF clone, which is shown in FIGS. 1A and 1B (SEQ ID NO:1), contains an open reading frame encoding a complete polypeptide of 157 amino acid residues, beginning in frame with a serine residue at the amino-terminal end of the polypeptide corresponding to nucleotide positions 2–4, and a predicted molecular weight of about 17.7 kDa. Nucleic acid molecules of the invention include those encoding the complete amino acid sequence shown in SEQ ID NO:2, or the complete amino acid sequence encoded by the cDNA clone in ATCC Deposit Number 209123, which molecules also can encode additional amino acids fused to the N-terminus of the HLF amino acid sequence.

The HLF protein of the present invention shares sequence homology with the translation product of the human mRNA for heregulin (FIG. 2; SEQ ID NO:3), including the following conserved domains: (a) the predicted extracellular domain of about 101 amino acids; (b) the predicted transmembrane domain of about 19 amino acids, and (c) the predicted intracellular domain of about 35 amino acids. Heregulin is thought to be important in oncogenesis. The homology between heregulin and HLF indicates that HLF may also be involved in oncogenesis.

Thus, one aspect of the invention provides an isolated nucleic acid molecule comprising a polynucleotide comprising a nucleotide sequence selected from the group consisting of: (a) a nucleotide sequence encoding the HLF polypeptide having the complete amino acid sequence in SEQ ID NO:2 (i.e., positions 1 to 157 of SEQ ID NO:2) or the complete amino acid sequence encoded by the cDNA clone contained in ATCC Deposit No. 209123; (b) a nucleotide sequence encoding the predicted extracellular domain of the HLF polypeptide having the amino acid sequence in SEQ ID NO:2 (i.e., positions 1 to 101 of SEQ ID NO:2) or as encoded by the cDNA clone contained in ATCC Deposit No. 209123; (c) a nucleotide sequence encoding the predicted transmembrane domain of the HLF polypeptide having the amino acid sequence in SEQ ID NO:2 (i.e., positions 102 to 121 of SEQ ID NO:2) or as encoded by the cDNA clone contained in ATCC Deposit No. 209123; (d) a nucleotide sequence encoding the predicted intracellular domain of the HLF polypeptide having the amino acid sequence in SEQ ID NO:2 (i.e., positions 122 to 157 of SEQ ID NO:2) or as encoded by the cDNA clone contained in ATCC Deposit No. 209123; (e) a nucleotide sequence encoding a soluble HLF polypeptide having the extracellular and intracellular domains but lacking the transmembrane domain; and (f) a nucleotide sequence complementary to any of the nucleotide sequences in (a) through (e) above.

Further embodiments of the invention include isolated nucleic acid molecules that comprise a polynucleotide having a nucleotide sequence at least 90% identical, and more preferably at least 95%, 96%, 97%, 98% or 99% identical to (or as stated in another way, a nucleotide sequence at most 10% different, and more preferably 5%, 4%, 3%, 2% or 1% different from), any of the nucleotide sequences in (a) through (f) above, or a polynucleotide which hybridizes under stringent hybridization conditions to a polynucleotide in (a) through (f) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a HLF polypeptide having an amino acid sequence in (a) through (e) above.

The present invention also relates to recombinant vectors, which include the isolated nucleic acid molecules of the present invention, and to host cells containing the recombinant vectors, as well as to methods of making such vectors and host cells and for using them for production of HLF polypeptides or peptides by recombinant techniques.

The invention further provides an isolated HLF polypeptide comprising an amino acid sequence selected from the group consisting of: (a) the amino acid sequence of the HLF polypeptide having the complete amino acid sequence shown in SEQ ID NO:2 (i.e., positions 1 to 157 of SEQ ID NO:2) or the complete amino acid sequence encoded by the cDNA clone contained in the ATCC Deposit No. 209123; (b) the amino acid sequence of the predicted extracellular domain of the HLF polypeptide having the amino acid sequence shown in SEQ ID NO:2 (i.e., positions 1 to 101 of SEQ ID NO:2) or as encoded by the cDNA clone contained in the ATCC Deposit No. 209123; (c) the amino acid sequence of the predicted transmembrane domain of the HLF polypeptide having the amino acid sequence shown in SEQ ID NO:2 (i.e., positions 102 to 121 of SEQ ID NO:2) or as encoded by the cDNA clone contained in the ATCC Deposit No. 209123; (d) the amino acid sequence of the predicted intracellular domain of the HLF polypeptide having the amino acid sequence shown in SEQ ID NO:2 (i.e., positions 122 to 157 of SEQ ID NO:2) or as encoded by the cDNA clone contained in the ATCC Deposit No. 209123; and (e) the amino acid sequence of a soluble HLF polypeptide having the extracellular and intracellular domains but lacking the transmembrane domain. The polypeptides of the present invention also include polypeptides having an amino acid sequence at least 80% identical (or at most 20% different), more preferably at least 90% identical (or at most 10% different), and still more preferably 95%, 96%, 97%, 98% or 99% identical to (or 5%, 4%, 3%, 2% or 1% different from) those described in (a), (b), (c), (d), or (e) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a HLF polypeptide having an amino acid sequence described in (a), (b), (c), (d), or (e) above. Peptides or polypeptides having the amino acid sequence of an epitope-bearing portion of a HLF polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a HLF polypeptide having an amino acid sequence described in (a), (b), (c), (d), or (e) above. The invention further provides methods for isolating antibodies that bind specifically to a HLF polypeptide having an amino acid sequence as described herein. Such antibodies are useful diagnostically or therapeutically as described below.

The invention also provides for pharmaceutical compositions comprising HLF polypeptides, particularly human HLF polypeptides, which may be employed, for instance, to treat many types of cancer. Methods of treating individuals in need of HLF polypeptides are also provided.

The invention further provides compositions comprising a HLF polynucleotide or an HLF polypeptide for administration to cells in vitro, to cells ex vivo and to cells in vivo, or to a multicellular organism. In certain particularly preferred embodiments of this aspect of the invention, the compositions comprise a HLF polynucleotide for expression of a HLF polypeptide in a host organism for treatment of disease. Particularly preferred in this regard is expression in a human patient for treatment of a dysfunction associated with aberrant endogenous activity of a HLF The present invention also provides a screening method for identifying compounds capable of enhancing or inhibiting a biological activity of the HLF polypeptide, which involves contacting a receptor which is inhibited or enhanced by the HLF polypeptide with the candidate compound in the presence of an HLF polypeptide, assaying changes in tyrosine phosphorylation states of the receptor and/or other molecules downstream in the corresponding signal transduction cascade in the presence of the candidate compound and of HLF polypeptide, and comparing the receptor activation state to a standard level, the standard being assayed when contact is made between the receptor and in the presence of the HLF polypeptide and the absence of the candidate compound In this assay, an increase in receptor activation state over the standard indicates that the candidate compound is an agonist of HLF activity and a decrease in receptor activation state compared to the standard indicates that the compound is an antagonist of HLF activity.

In another aspect, a screening assay for agonists and antagonists is provided which involves determining the effect a candidate compound has on HLF binding to a receptor. In particular, the method involves contacting the receptor with an HLF polypeptide and a candidate compound and determining whether HLF polypeptide binding to the receptor is increased or decreased due to the presence of the candidate compound. In this assay, an increase in binding of HLF over the standard binding indicates that the candidate compound is an agonist of HLF binding activity and a decrease in HLF binding compared to the standard indicates that the compound is an antagonist of HLF binding activity.

It has been discovered that HLF is expressed only in the amygdala, whole brain, and primary breast culture tissue. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the neural system, significantly higher or lower levels of HLF gene expression may be detected in certain tissues (e.g., cancerous and wounded tissues) or bodily fluids (e.g., serum, plasma, urine, synovial fluid or spinal fluid) taken from an individual having such a disorder, relative to a "standard" HLF gene expression level, i.e., the HLF expression level in healthy tissue from an individual not having the neural system disorder. Thus, the invention provides a diagnostic method useful during diagnosis of such a disorder, which involves: (a) assaying HLF gene expression level in cells or body fluid of an individual; (b) comparing the HLF gene expression level with a standard HLF gene expression level, whereby an increase or decrease in the assayed HLF gene expression level compared to the standard expression level is indicative of disorder in the neural system.

An additional aspect of the invention is related to a method for treating an individual in need of an increased level of HLF activity in the body comprising administering to such an individual a composition comprising a therapeutically effective amount of an isolated HLF polypeptide of the invention or an agonist thereof.

A still further aspect of the invention is related to a method for treating an individual in need of a decreased level of HLF activity in the body comprising, administering to such an individual a composition comprising a therapeutically effective amount of an HLF antagonist. Preferred antagonists for use in the present invention are HLF-specific antibodies.

BRIEF DESCRIPTION OF THE FIGURES

FIGS. 1A and 1B shows the nucleotide sequence (SEQ ID NO:1) and deduced amino acid sequence (SEQ ID NO:2) of HLF. An extracellular epidermal growth factor (EGF) domain, conserved in many other EGF-like polypeptides, is underlined in FIGS. 1A and 1B.

FIG. 2 shows the regions of identity between the amino acid sequences of the HLF protein and translation product of the human mRNA for heregulin (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 5 shows the amino acid sequences of the EGF/heregulin family of growth factors and of the NRG-3 novel sequences. Cysteines (C) defining the basic structure of the EGF domain and highly conserved amino acids are in bold. Listed are sequences for the EGF-like domains of transforming growth factor (TGF)-alpha (SEQ ID NO:11); epidermal growth factor (EGF; SEQ ID NO:12); heparin-binding EGF (HB-EGF; SEQ ID NO:13); amphiregulin (Amph; SEQ ID NO:14); beta-cellulin (beta-cellulin; SEQ ID NO:15); neuregulin (neuR; SEQ ID NO:16); human heregulins 1-alpha (HRG-alpha-1; SEQ ID NO:17) and 1-beta (HRG-beta-1; SEQ ID NO:18); heregulin-related gene (HRG)-2 (SEQ ID NO:19); and amino acids 29–80 of HLF of the present invention (amino acids 29–80 of SEQ ID NO:2).

DETAILED DESCRIPTION

Figure 3:
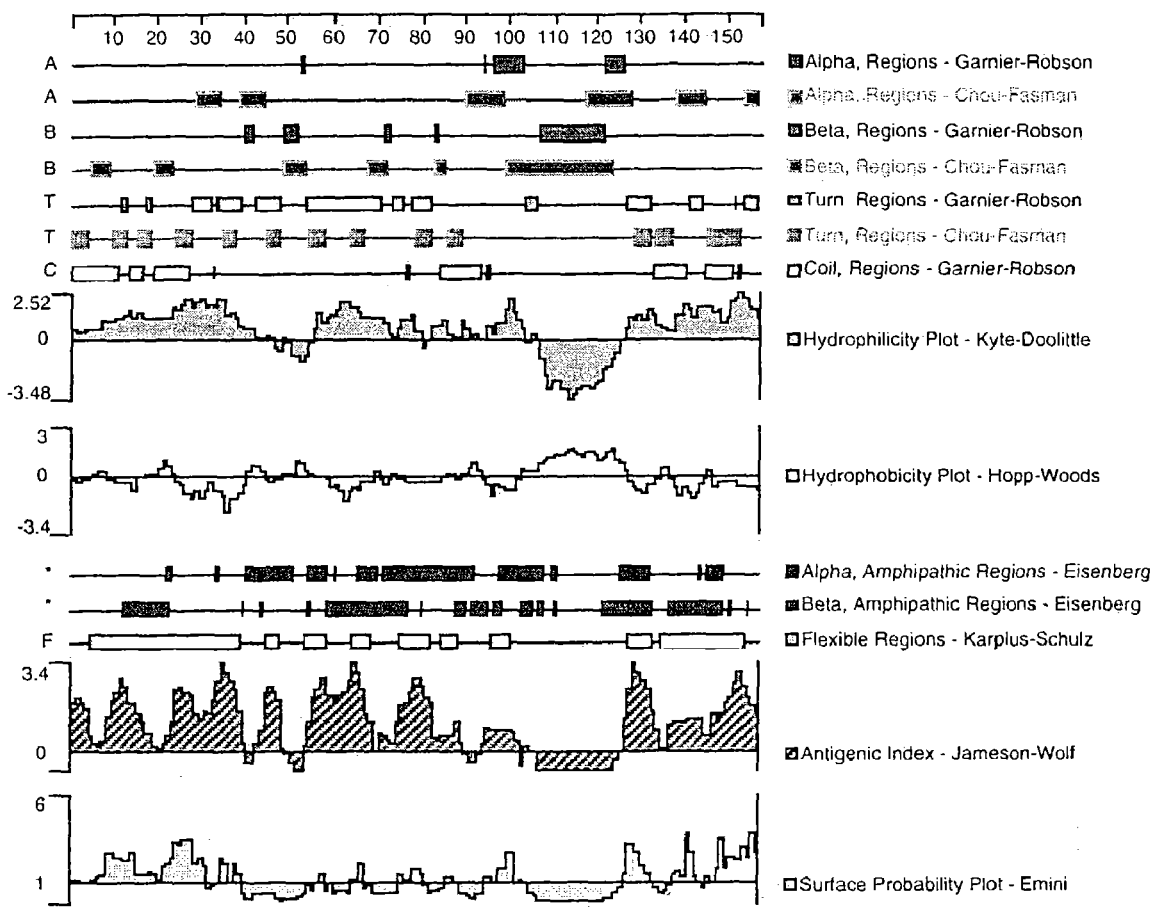
FIG. 3 shows an analysis of the HLF amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the HLF protein, i.e., regions from which epitope-bearing peptides of the invention can be obtained.

The present invention provides isolated nucleic acid molecules comprising a polynucleotide encoding a HLF polypeptide having the amino acid sequence shown in SEQ ID NO:2, which was determined by sequencing a cloned cDNA. The nucleotide sequence shown in FIGS. 1A and 1B (SEQ ID NO:1) was obtained by sequencing the HAGFE38 clone, which was deposited on Jun. 19, 1997 at the American Type Culture Collection, 12301 Park Lawn Drive, Rockville, Md. 20852 (the ATCC is now located at 10801 University Blvd., Manassas, Va. 20110–2209), and given accession number ATCC 209123. The deposited clone is contained in the pBluescript SK(−) plasmid (Stratagene, La Jolla, Calif.).

The HLF protein of the present invention shares sequence homology with the translation product of the human mRNA for heregulin (FIG. 2; SEQ ID NO:3). Heregulin is thought to be an important molecule in the activation pathways of the erbB family of cell surface receptors. Altered expression of heregulin and related ligand molecules, and/or the erbB family of receptor molecules can often lead to the loss of regulation of cellular growth and ultimately to oncogenesis. For example, the neu differentiation factor (NDF) is a homologue of both heregulin and HLF. NDF is a neuron/glia-specific signaling molecule which has been observed to regulate survival, proliferation, and maturation of Schwann cell precursors (Dong, Z., et al., *Neuron* 15:585–596; 1995; Marchionni, M. A., et al., *Nature* 362:312–318; 1993). HLF is a member of the same heregulin family of proteins and has, at least, activities similar to those described above for heregulin and NDF.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any-DNA sequence determined by this automated approach, any nucleotide sequence determined herein may contain some errors. Nucleotide sequences determined by automation are typically at least about 90% identical (or 10% different), more typically at least about 95% to at least about 99.9% identical to (or at most about 5% to at most about 0.1% different from) the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and 1B (SEQ ID NO:1), a nucleic acid molecule of the present invention encoding a HLF polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from human amygdala.

The determined nucleotide sequence of the HLF cDNA of FIGS. 1A and 1B (SEQ ID NO:1) contains an open reading frame encoding a protein of 157 amino acid residues, with an amino-terminal serine codon at nucleotide positions 2–4 of the nucleotide sequence in FIG. 1A (SEQ ID NO:1), and a deduced molecular weight of about 17.7 kDa. The amino acid sequence of the HLF protein shown in SEQ ID NO:2 is about 32.7% identical to human mRNA for heregulin (FIG. 2). The nucleotide and amino acid sequence of human heregulin has been reported by Holmes and colleagues (Science 256:1205–1210; 1992; GenBank Accession No. M94166).

The open reading frame of the HLF gene shares sequence homology with the translation product of the human mRNA for heregulin (FIG. 2; SEQ ID NO:3), including the conserved EGF domain in HLF of about 67 amino acids (amino acids 26–93 of SEQ ID NO:2). Heregulin is thought to be important in the regulation of the activation state of the erbB family of cell surface receptors, in the regulation of cellular growth control, and ultimately in the regulation of oncogenesis. The homology between heregulin and HLF indicates that HLF may also be involved in the regulation of the activation state of the erbB family of cell surface receptors, in the regulation of cellular growth control, and ultimately in the regulation of oncogenesis.

As one of ordinary skill would appreciate, due to the possibilities of sequencing errors discussed above, the actual complete HLF polypeptide encoded by the deposited cDNA, which comprises about 157 amino acids, may be somewhat longer or shorter. More generally, the actual open reading frame may be anywhere in the range of ±100 amino acids, ±20 amino acids, more likely in the range of ±10 amino acids, of that predicted from the serine codon at the N-terminus shown in FIG. 1A (SEQ ID NO:1). It will further be appreciated that, depending on the analytical criteria used for identifying various functional domains, the exact "address" of the extracellular, EGF, transmembrane, and intracellular domains of the HLF polypeptide may differ slightly from the predicted positions above. For example, the exact location of the HLF EGF domain in SEQ ID NO:2 may vary slightly (e.g., the address may "shift" by about 1 to about 20 residues, more likely about 1 to about 5 residues) depending on the criteria used to define the domain. In this case, the ends of the transmembrane domain and the beginning of the EGF domain were predicted on the basis of the identification of the conserved cysteine residues at positions 35, 43, 49, 62, 64, and 73 of SEQ ID NO:2, as shown in FIG. 1A. In any event, as discussed further below, the invention further provides polypeptides having various residues deleted from the N-terminus of the complete polypeptide, including polypeptides lacking one or more amino acids from the N-terminus of the extracellular EGF domain described herein, which constitute soluble forms of the extracellular EGF domain of the HLF protein.

Leader and Mature Sequences

In addition, methods for predicting whether a protein has a secretory leader as well as the cleavage point for that leader sequence are available. For instance, the method of McGeoch (Virus Res. 3:271–286; 1985) uses the information from a short N-terminal charged region and a subsequent uncharged region of the complete (uncleaved) protein. The method of von Heinje (Nucleic Acids Res. 14:4683–4690; 1986) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete HLF polypeptide was analyzed by the computer program PSORT, available from Dr. Kenta Nakai of the Institute for Chemical Research, Kyoto University (Nakai, K. and Kanehisa, M., Genomics 14:897–911; 1992), which is an expert system for predicting the cellular location of a protein based on the amino acid sequence. As part of this computational prediction of localization, the methods of McGeoch and von Heinje are incorporated. The analysis of the HLF amino acid sequence by this program indicated that there appears to be no N-terminal signal sequence associated with the HLF amino acid sequence shown in SEQ ID NO:2, and that the HLF molecule, as shown in SEQ ID NO:2, appears to be a type Ib membrane protein.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) beginning in frame with a serine codon at positions 2–4 of the nucleotide sequence shown in FIG. 1A (SEQ ID NO:1).

In addition, isolated nucleic acid molecules of the invention include DNA molecules which comprise a sequence substantially different from those described above but which, due to the degeneracy of the genetic code, still encode the HLF protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as E. coli).

In another aspect, the invention provides isolated nucleic acid molecules encoding the HLF polypeptide having an amino acid sequence encoded by the cDNA clone contained in the plasmid deposited as ATCC Deposit No. 209123 on Jun. 19, 1997.

The invention further provides an isolated nucleic acid molecule having the nucleotide sequence shown in FIGS. 1A and 1B (SEQ ID NO:1) or the nucleotide sequence of the HLF cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the HLF gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–2199 of SEQ ID NO:1.

In addition, the invention provides nucleic acid molecules having nucleotide sequences related to a portion of SEQ ID NO:1 which has been determined from the following related cDNA clone: HAGFE38R.

Further, the invention includes a polynucleotide comprising any portion of at least about 30 nucleotides, preferably at least about 50 nucleotides, of SEQ ID NO:1 from residue about 1 to about 220 and from about 400 to 2199. More preferably, the invention includes a polynucleotide comprising nucleotide residues 1 to 2199, 1 to 1500, 1 to 1000, 1 to 500, 1 to 250, 250 to 2199, 250 to 1500, 250 to 1000, 250 to 500, 500 to 2199, 500 to 1500, 500 to 1000, 1000 to 2199, and 1000 to 1500.

More generally, by a fragment of an isolated nucleic acid molecule having the nucleotide sequence of the deposited cDNA or the nucleotide sequence shown in FIGS. 1A and 1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A and 1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and 1B (SEQ ID NO:1). Preferred nucleic acid fragments of the present invention include nucleic acid molecules encoding epitope-bearing portions of the HLF polypeptide as identified in FIG. 3 and described in more detail below. Preferred nucleic acid fragments of the present invention also include nucleic acid molecules encoding Garnier-Robson and/or Chou-Fasman alpha, beta, and/or turn regions, Garnier-Robson coil regions, Kyte-Doolittle hydrophilic regions, Hopp-Woods hydrophobic regions, Eisenberg alpha and/or beta amphipathic regions, Karplus-Schulz flexible regions, Jameson-Wolf antigenic regions, and/or Emini surface probability regions of the HLF polypeptide as identified in FIG. 3 or in a tabular representation of the data presented in FIG. 3.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209123, or, for example, any specific HLF polynucleotide fragment described above (a non-limiting example is a Chou-Fasman alpha turn region). By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and 1B (SEQ ID NO:1)). Of course, a polynucleotide which hybridizes only to a poly A sequence (such as the 3' terminal poly(A) tract of the HLF cDNA shown in FIG. 1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an HLF polypeptide may include, but are not limited to those encoding the amino acid sequence of the complete polypeptide, by itself; and the coding sequence for the complete polypeptide and additional sequences, such as those encoding an added secretory leader sequence, such as a pre-, or pro- or prepro-protein sequence.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the HLF fused to Fc at the N- or C-terminus.

Variant and Mutant Polynucleotides

The present invention further relates to variants of the nucleic acid molecules of the present invention, which encode portions, analogs or derivatives of the HLF protein. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the HLF protein or portions thereof. Also especially preferred in this regard are conservative substitutions.

Most highly preferred are nucleic acid molecules encoding the EGF domain of the protein having the amino acid sequence shown in SEQ ID NO:2 or the EGF domain of the HLF amino acid sequence encoded by the deposited cDNA clone (nucleotides 77–280 of SEQ ID NO:1).

Thus, one aspect of the invention provides an isolated nucleic acid molecule comprising a polynucleotide having a nucleotide sequence selected from the group consisting of: (a) a nucleotide sequence encoding the HLF polypeptide having the complete amino acid sequence in SEQ ID NO:2 (i.e., positions 1 to 157 of SEQ ID NO:2) or the complete amino acid sequence encoded by the cDNA clone contained in ATCC Deposit No. 209123; (b) a nucleotide sequence encoding the predicted extracellular domain of the HLF polypeptide having the amino acid sequence in SEQ ID NO:2 (i.e., positions 1 to 101 of SEQ ID NO:2) or as encoded by the cDNA clone contained in ATCC Deposit No. 209123; (c) a nucleotide sequence encoding the predicted transmembrane domain of the HLF polypeptide having the amino acid sequence in SEQ ID NO:2 (i.e., positions 102 to 121 of SEQ ID NO:2) or as encoded by the cDNA clone contained in ATCC Deposit No. 209123; (d) a nucleotide sequence encoding the predicted intracellular domain of the HLF polypeptide having the amino acid sequence in SEQ ID NO:2 (i.e., positions 122 to 157 of SEQ ID NO:2) or as encoded by the cDNA clone contained in ATCC Deposit No. 209123; (e) a nucleotide sequence encoding a soluble HLF polypeptide having the extracellular and intracellular domains but lacking the transmembrane domain; and (f) a nucleotide sequence complementary to any of the nucleotide sequences in (a) through (e) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e) or (f), above, or a polynucleotide which hybridizes under stringent hybridization conditions to a polynucleotide in (a), (b), (c), (d), (e) or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of an HLF polypeptide having an amino acid sequence in (a), (b), (c), (d) or (e), above., The present invention also relates to recombinant vectors, which include the isolated nucleic acid molecules of the present invention, and to host cells containing the recombinant vectors, as well as to methods of making such vectors and host cells and for using them for production of HLF polypeptides or peptides by recombinant techniques.

By a polynucleotide having a nucleotide sequence at least, for example, 95% "identical" to a reference nucleotide sequence encoding an HLF polypeptide is intended that the nucleotide sequence of the polynucleotide is identical to the reference sequence except that the polynucleotide sequence may include up to five point mutations per each 100 nucleotides of the reference nucleotide sequence encoding the HLF polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to (or at most 10%, 5%, 4%, 3%, 2% or 1% different from), for instance, the nucleotide sequence shown in FIGS. 1A and 1B or to the nucleotide's sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

By a polynucleotide having a nucleotide sequence at least, for example, 95% "identical" to (or 5% different from) a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the HLF polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in SEQ ID NO:1, the ORF (open reading frame), or any fragment specified as described herein.

As a practical matter, whether any particular nucleic acid molecule or polypeptide is at least 90%, 95%, 96%, 97%, 98% or 99% identical to (or at most 10%, 5%, 4%, 3%, 2% or 1% different from) a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

The present application is directed to nucleic acid molecules at least 90%, 95%, 96%, 97%, 98% or 99% identical to (or at most 10%, 5%, 4%, 3%, 2% or 1% different from) the nucleic acid sequence shown in FIGS. 1A and 1B (SEQ ID NO:1) or to the nucleic acid sequence of the deposited cDNA, irrespective of whether they encode a polypeptide having HLF activity. This is because even where a particular nucleic acid molecule does not encode a polypeptide having HLF activity, one of skill in the art would still know how to use the nucleic acid molecule, for instance, as a hybridization probe or a polymerase chain reaction (PCR) primer. Uses of the nucleic acid molecules of the present invention that do not encode a polypeptide having HLF activity include, inter alia, (1) isolating the HLF gene or allelic variants thereof in a cDNA library; (2) in situ hybridization (e.g., "FISH") to metaphase chromosomal spreads to provide precise chromosomal location of the HLF gene, as described in Verma et al., Human Chromosomes: A Manual of Basic Techniques, Pergamon Press, New York (1988); and Northern Blot analysis for detecting HLF mRNA expression in specific tissues.

Preferred, however, are nucleic acid molecules having sequences at least 90%, 95%, 96%, 97%, 98% or 99% identical to (or at most 10%, 5%, 4%, 3%, 2% or 1% different from) the nucleic acid sequence shown in FIGS. 1A and 1B (SEQ ID NO:1) or to the nucleic acid sequence of the deposited cDNA which do, in fact, encode a polypeptide having HLF protein activity. By "a polypeptide having HLF activity" is intended polypeptides exhibiting activity similar, but not necessarily identical, to an activity of the full-length or soluble EGF domain of the HLF protein of the invention, as pleasured in a particular biological assay. For example, the HLF protein of the present invention can be assayed for activity by analyzing changes in the phosphorylation state cell surface receptors. As described by Marchionni and colleagues (Nature 362:312–318; 1993), a tyrosine kinase activation assay may be used to determine such activity. In this assay, a wide variety of cells and cell lines are allowed to become quiescent in low serum medium. HLF protein, or variants thereof, may then be added exogenously to the growth medium. Cultured cells are then lysed in an SDS-based lysis buffer and subject to SDS-PAGE. The proteins separated by SDS-PAGE are then transferred to a membrane and immunoblotted with an anti-phosphotyrosine antibody. Changes in tyrosine phosphorylation state of cell surface receptor molecules may then be assessed by comparing immunoblots of cell samples which were treated or not treated with HLF, or a variant thereof. Such activity is useful for determining the affect of HLF, or variants thereof, on the stimulation of a wide variety of cell surface receptor molecules and determining which signal transduction cascades may be initiated by the binding of HLF, or a variant thereof.

HLF protein binding modulates the tyrosine phosphorylation state and initiates a variety of signal transduction cascades in erbB family or other cell surface receptor molecules in a dose-dependent manner in the above-described assay. Thus, "a polypeptide having HLF protein activity" includes polypeptides that also exhibit any of the same binding and phosphorylation state altering activities in the above-described assays in a dose-dependent manner. Although the degree of dose-dependent activity need not be identical to that of the HLF protein, preferably, "a polypeptide having HLF protein activity" will exhibit substantially similar dose-dependence in a given activity as compared to the HLF protein (i.e., the candidate polypeptide will exhibit greater activity or not more than about 25-fold less and, preferably, not more than about tenfold less activity relative to the reference HLF protein).

In addition, the binding of HLF, or variants thereof, to a particular receptor molecule may be assayed by cross-linking HLF, or an HLF variant, to whichever receptor it binds on the cell surface and then immunoprecipitating the resulting ligand/receptor complex with a specific antiserum. Such an assay will thereby indicate a specific receptor binding profile for the HLF protein(s). As described by Holmes and colleagues (*Science* 256:1205–1210; 1992), $^{125}$I-labeled HLF, or HLF variant, protein is cross-linked to any of a variety of cells or cell lines by incubating a suspension of cells and $10^6$ CPM of $^{125}$I-labeled HLF, or HLF variant, proteins in Hank's balanced salts (Life Technologies, Inc., Rockville, Md.) for 30 minutes at 22° C. Bis(sulfosuccinimidyl) suberate is added to the cell suspensions to a final concentration of 1 mM and the suspensions are incubated for an additional 30 minutes. Cells are washed Tris-buffered saline (TBS) and then lysed in TBS containing Triton X-100 (0.5%). Immunoprecipitations are then performed using portions of treated and mock-treated cultures combined with antisera to specific cellular receptor molecules. Samples are then prepared in SDS sample buffer, analyzed by SDS-PAGE (5.5% polyacrylamide gels), and visualized by autoradiography.

Of course, due to the degeneracy of the genetic code, one of ordinary skill in the art will immediately recognize that a large number of the nucleic acid molecules having a sequence at least 90%, 95%, 96%, 97%, 98%, or 99% identical to (or at most 10%, 5%, 4%, 3%, 2% or 1% different from) the nucleic acid sequence of the deposited cDNA or the nucleic acid sequence shown in FIGS. 1A and 1B (SEQ ID NO:1) will encode a polypeptide "having HLF protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having HLF protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of HLF polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the DNA of the invention is operatively associated with an appropriate heterologous regulatory element (e.g. a promoter and/or enhancer), such as the phage lambda PL promoter, the *E. coli* lac, trp, phoA and tac promoters, the SV40 early and late promoters and promoters of retroviral LTRs, to name a few. Other suitable promoters and enhancers will be known to the skilled artisan.

In embodiments in which vectors contain expression constructs, these constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein (comprising the polypeptide joined via a peptide bond to a heterologous protein sequence (of a different protein)), and may include not only secretion signals, but also additional heterologous functional regions. Such a protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g. by use of a peptide synthesizer. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The HLF protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated HLF polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of HLF polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268: 2984–2988; 1993) reported modified KGF proteins that had heparin binding activity even if 3, 8, or 27 amino-terminal amino acid residues were missing. In the present case, since the protein of the invention is a member of the EGF polypeptide family, deletions of N-terminal amino acids up to the cysteine at position 35 of SEQ ID NO:2 may retain some biological activity such as receptor binding and the initiation of the corresponding signal transduction cascade. Polypeptides having further N-terminal deletions including the cysteine residue at position 35 of SEQ ID NO:2 would not be expected to retain such biological activities because it is known that this residue in an EGF-like, or heregulin, polypeptide is one of six conserved cysteine residues required for both structure and biological activity. That is to say, the first cysteine is required for forming one of several disulfide bridges needed to provide structural stability which is, in turn, necessary for receptor binding and the instantiation of the signal transduction cascade.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or extracellular domain of the protein generally will be retained when less than the majority of the residues of the complete or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of HLF shown in SEQ ID NO:2, up to the cysteine residue at position number 35, and polynucleotides encoding such polypeptides. In particular, the present invention provides polypeptides comprising the amino acid sequence of residues n-35 of SEQ ID NO:2, where n is an integer in the range of 1–35, and 35 is the position of the first residue from the N-terminus of the complete HLF polypeptide (shown in SEQ ID NO:2) believed to be required for the HLG protein to bind its receptor and initiate the corresponding signal transduction cascade.

More in particular, the invention provides polynucleotides encoding polypeptides comprising, or alternatively consisting of, the amino acid sequence of residues of 1-157, 2-57, 3-157, 4-157, 5-157, 6-157, 7-157, 8-157, 9-157, 10-157, 11-157, 12-157, 13-157, 14-157, 15-157, 16-157, 17-157, 18-157, 19-157, 20-157, 21-157, 22-157, 23-157, 24-157, 25-157, 26-157, 27-157, 28-157, 29-157, 30-157, 31-157, 32-157, 33-157, 34-157, and 35-157 of SEQ ID NO:2. Polynucleotides encoding these polypeptides also are provided.

Similarly, many examples of biologically functional C-terminal deletion muteins are known. For instance, Interferon-gamma shows up to ten times higher activities by deleting 8–10 amino acid residues from the carboxy terminus of the protein (Dobeli et al., *J. Biotechnology* 7:199–216; 1988). In the present case, since the protein of the invention is a member of the EGF or heregulin-like polypeptide family, deletions of C-terminal amino acids up to the most carboxy-terminal cysteine of the extracellular domain (position 73 of SEQ ID NO:2) may retain some biological activity such as such as receptor binding and the initiation of the corresponding signal transduction cascade. Polypeptides having further C-terminal deletions including the cysteine residue at position 73 of SEQ ID NO:2 would not be expected to retain such biological activities because it is known that this residue in an EGF-like, or heregulin-like, polypeptide is one of six conserved cysteine residues required for both structure and biological activity. That is to say, the first cysteine is required for forming one of several disulfide bridges needed to provide structural stability which is, in turn, necessary for receptor binding and the instantiation of the signal transduction cascade.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or extracellular domain of the protein generally will be retained when less than the majority of the residues of the complete or extracellular domain protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the HLF shown in SEQ ID NO:2, up to the cysteine residue at position 73 of SEQ ID NO:2, and polynucleotides encoding such polypeptides. In particular, the present invention provides polypeptides having the amino acid sequence of residues 1-m of the amino acid sequence in SEQ ID NO:2, where m is any integer in the range of 73 to 101, and residue 73 is the position of the first residue from the C-terminus of the complete HLF polypeptide (shown in SEQ ID NO:2) believed to be required for receptor binding and initiation of the corresponding signal transduction cascade.

More in particular, the invention provides polynucleotides encoding polypeptides comprising, or alternatively consisting of, the amino acid sequence of residues 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, and 1-101 of SEQ ID NO:2. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above.

Also included are a nucleotide sequence encoding a polypeptide consisting of a portion of the complete HLF amino acid sequence encoded by the cDNA clone contained in ATCC Deposit No. 209123, where this portion excludes from 1 to about 34 amino acids from the amino terminus of the complete amino acid sequence encoded by the cDNA clone contained in ATCC Deposit No. 209123, or from 1 to about 83 amino acids from the carboxy terminus, or any combination of the above amino terminal and carboxy terminal deletions, of the complete amino acid sequence encoded by the cDNA clone contained in ATCC Deposit No. 209123. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened HLF mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that an HLF mutein with a large number of deleted N-terminal amino acid residues may retain some biological or immunogenic activities. In fact, peptides composed of as few as six HLF amino acid residues may often evoke an immune response.

Accordingly, the present invention further provides polypeptides having one or more residues deleted from the amino terminus of the amino acid sequence of the HLF shown in SEQ ID NO:2, up to the asparagine residue at position number 152 and polynucleotides encoding such polypeptides. In particular, the present invention provides polypeptides comprising the amino acid sequence of residues n'-152 of SEQ ID NO:2, where n' is an integer in the range of 2-152, and 153 is the position of the first residue from the N-terminus of the complete HLF polypeptide believed to be required for at least immunogenic activity of the HLF protein.

More in particular, the invention provides polynucleotides encoding polypeptides comprising, or alternatively consisting of, the amino acid sequence of residues of S-2 to K-157; S-3 to K-157; S-4 to K-157; S-5 to K-157; A-6 to K-157; T-7 to K-157; T-8 to K-157; T-9 to K-157; T-10 to K-157; P-11 to K-157; E-12 to K-157; T-13 to K-157; S-14 to K-157; T-15 to K-157; S-16 to K-157; P-17 to K-157; K-18 to K-157; F-19 to K-157; H-20 to K-157; T-21 to K-157; T-22 to K-157; T-23 to K-157; Y-24 to K-157; S-25 to K-157; T-26 to K-157; E-27 to K-157; R-28 to K-157; S-29 to K-157; E-30 to K-157; H-31 to K-157; F-32 to K-157; K-33 to K-157; P-34 to K-157; C-35 to K-157; R-36 to K-157; D-37 to K-157; K-38 to K-157; D-39 to K-157; L-40 to K-157; A-41 to K-157; Y-42 to K-157; C-43 to K-157; L-44 to K-157; N-45 to K-157; D-46 to K-157; G-47 to K-157;

E-48 to K-157; C-49 to K-157; F-50 to K-157; V-51 to K-157; I-52 to K-157; E-53 to K-157; T-54 to K-157; L-55 to K-157; T-56 to K-157; G-57 to K-157; S-58 to K-157; H-59 to K-157; K-60 to K-157; H-61 to K-157; C-62 to K-157; R-63 to K-157; C-64 to K-157; K-65 to K-157; E-66 to K-157; G-67 to K-157; Y-68 to K-157; Q-69 to K-157; G-70 to K-157; V-71 to K-157; R-72 to K-157; C-73 to K-157; D-74 to K-157; Q-75 to K-157; F-76 to K-157; L-77 to K-157; P-78 to K-157; K-79 to K-157; T-80 to K-157; D-81 to K-157; S-82 to K-157; I-83 to K-157; L-84 to K-157; S-85 to K-157; D-86 to K-157; P-87 to K-157; N-88 to K-157; H-89 to K-157; L-90 to K-157; G-91 to K-157; I-92 to K-157; E-93 to K-157; F-94 to K-157; M-95 to K-157; E-96 to K-157; S-97 to K-157; E-98 to K-157; E-99 to K-157; V-100 to K-157; Y-101 to K-157; Q-102 to K-157; R-103 to K-157; Q-104 to K-157; V-105 to K-157; L-106 to K-157; S-107 to K-157; I-108 to K-157; S-109 to K-157; C-110 to K-157; I-111 to K-157; I-112 to K-157; F-113 to K-157; G-114 to K-157; I-115 to K-157; V-116 to K-157; I-117 to K-157; V-118 to K-157; G-119 to K-157; M-120 to K-157; F-121 to K-157; C-122 to K-157; A-123 to K-157; A-124 to K-157; F-125 to K-157; Y-126 to K-157; F-127 to K-157; K-128 to K-157; S-129 to K-157; K-130 to K-157; R-131 to K-157; N-132 to K-157; I-133 to K-157; T-134 to K-157; A-135 to K-157; N-136 to K-157; S-137 to K-157; V-138 to K-157; S-139 to K-157; E-140 to K-157; E-141 to K-157; R-142 to K-157; W-143 to K-157; K-144 to K-157; G-145 to K-157; L-146 to K-157; P-147 to K-157; S-148 to K-157; Q-149 to K-157; E-150 to K-157; P-151 to K-157; and N-152 to K-157 of the HLF sequence shown in SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened HLF mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that an HLF mutein with a large number of deleted C-terminal amino acid residues may retain some biological or immunogenic activities. In fact, peptides composed of as few as six HLF amino acid residues may often evoke an immune response.

Accordingly, the present invention further provides polypeptides having one or more residues deleted from the carboxy terminus of the amino acid sequence of the HLF shown in SEQ ID NO:2, up to the alanine residue at position number 6, and polynucleotides encoding such polypeptides. In particular, the present invention provides polypeptides comprising the amino acid sequence of residues 1-m' of SEQ ID NO:2, where m' is an integer in the range of 7–156, and 6 is the position of the first residue from the C-terminus of the complete HLF polypeptide believed to be required, for at least immunogenic activity of the HLF protein.

More in particular, the invention provides polynucleotides encoding polypeptides comprising, or alternatively consisting of, the amino acid sequence of residues 1 to D-156; S-1 to Q-155; S-1 to Q-154; S-1 to L-153; S-1 to N-152; S-1 to P-151; S-1 to E-150; S-1 to Q-149; S-1 to S-148; S-1 to P-147; S-1 to L-146; S-1 to G-145; S-1 to K-144; S-1 to W-143; S-1 to R-142; S-1 to E-141; S-1 to E-140; S-1 to S-139; S-1 to V-138; S-1 to S-137; S-1 to N-136; S-1 to A-135; S-1 to T-134; S-1 to I-133; S-1 to N-132; S-1 to R-131; S-1 to K-130; S-1 to S-129; S-1 to K-128; S-1 to F-127; S-1 to Y-126; S-1 to F-125; S-1 to A-124; S-1 to A-123; S-1 to C-122; S-1 to F-121; S-1 to M-120; S-1 to G-119; S-1 to V-118; S-1 to I-117; S-1 to V-116; S-1 to I-115; S-1 to G-114; S-1 to F-113; S-1 to I-112; S-1 to I-111; S-1 to C-110; S-1 to S-109; S-1 to I-108; S-1 to S-107; S-1 to L-106; S-1 to V-105; S-1 to Q-104; S-1 to R-103; S-1 to Q-102; S-1 to Y-101; S-1 to V-100; S-1 to E-99; S-1 to E-98; S-1 to S-97; S-1 to E-96; S-1 to M-95; S-1 to F-94; S-1 to E-93; S-1 to I-92; S-1 to G-91; S-1 to L-90; S-1 to H-89; S-1 to N-88; S-1 to P-87; S-1 to D-86; S-1 to S-85; S-1 to L-84; S-1 to I-83; S-1 to S-82; S-1 to D-81; S-1 to T-80; S-1 to K-79; S-1 to P-78; S-1 to L-77; S-1 to F-76; S-1 to Q-75; S-1 to D-74;, S-1 to C-73; S-1 to R-72; S-1 to V-71; S-1 to G-70; S-1 to Q-69; S-1 to Y-68; S-1 to G-67; S-1 to E-66; S-1 to K-65; S-1 to C-64; S-1 to R-63; S-1 to C-62; S-1 to H-61; S-1 to K-60; S-1 to H-59; S-1 to S-58; S-1 to G-57; S-1 to T-56; S-1 to L-55; S-1 to T-54; S-1 to E-53; S-1 to I-52; S-1 to V-51; S-1 to F-50; S-1 to C-49; S-1 to E-48; S-1 to G-47; S-1 to D-46; S-1 to N-45; S-1 to L-44; S-1 to C-43; S-1 to Y-42; S-1 to A-41; S-1 to L-40; S-1 to D-39; S-1 to K-38; S-1 to D-37; S-1 to R-36; S-1 to C-35; S-1 to P-34; S-1 to K-33; S-1 to F-32; S-1 to H-31; S-1 to E-30; S-1 to S-29; S-1 to R-28; S-1 to E-27; S-1 to T-26; S-1 to S-25; S-1 to Y-24; S-1 to T-23; S-1 to T-22; S-1 to T-21; S-1 to H-20; S-1 to F-19; S-1 to K-18; S-1 to P-17; S-1 to S-16; S-1 to T-15; S-1 to S-14; S-1 to T-13; S-1 to E-12; S-1 to P-11; S-1 to T-10; S-1 to T-9; S-1 to T-8; S-1 to T-7; S-1 to A-6 of the HLF sequence shown in SEQ ID NO:2. Polynucleotides encoding these polypeptides also are provided.

The invention also provides polypeptides having one or more amino acids deleted from both the amino and the carboxyl termini of an HLF polypeptide, which may be described generally as having residues n'-m' of SEQ ID NO:2, where n' and m' are integers as described above.

Also as mentioned above, even if deletion of one or more amino acids from the N-terminus of a protein results in modification of loss of one or more biological functions of the protein, other biological activities may still be retained. Thus, the ability of the shortened HLF mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that an HLF mutein with a large number of deleted N-terminal amino acid residues may retain some biological or immunogenic activities. In fact, peptides composed of as few as six HLF amino acid residues may often evoke an immune response.

Accordingly, the present invention further provides polypeptides having one or more residues deleted from the amino terminus of the amino acid sequence of the HLF show n in SEQ ID NO:22, up to the aspartic acid residue at position number 715 and polynucleotides encoding such polypeptides. In particular, the present invention provides polypeptides comprising the amino acid sequence of residues n"-715 of SEQ ID NO:22, where n" is an integer in the range of 2–715, and 716 is the position of the first residue from the N-terminus of the complete HLF polypeptide believed to be required for at least immunogenic activity of the HLF protein.

More in particular, the invention provides polynucleotides encoding polypeptides comprising, or alternatively consisting of, the amino acid sequence of residues of S-2 to K-720; E-3 to K-720; G-4 to K-720; A-5 to K-720; A-6 to K-720; A-7 to K-720; A-8 to K-720; S-9 to K-720; P-10 to K-720; P-11 to K-720; G-12 to K-720; A-13 to K-720; A-14 to K-720; S-15 to K-720; A-16 to K-720; A-17 to K-720; A-18 to K-720; A-19 to K-720; S-20 to K-720; A-21 to K-720; E-22 to K-720; E-23 to K-720; G-24 to K-720; T-25 to K-720; A-26 to K-720; A-27 to K-720; A-28 to K-720; A-29 to K-720; A-30 to K-720; A-31 to K-720; A-32 to K-720; A-33 to K-720; A-34 to K-720; G-35 to K-720; G-36 to K-720; G-37-to K-720; P-38 to K-720; D-39 to K-720; G-40 to K-720; G-41 to K-720; G-42 to K-720; E-43 to K-720; G-44 to K-720; A-45 to K-720; A-46 to K-720; E-47 to K-720; P-48 to K-720; P-49 to K-720; R-50 to K-720; E-51 to K-720; L-52 to K-720; R-53 to K-720; C-54 to K-720; S-55 to K-720; D-56 to K-720; C-57 to K-720; I-58 to K-720; V-59 to K-720; W-60 to K-720; N-61 to K-720; R-62 to K-720; Q-63 to K-720; Q-64 to K-720; T-65 to K-720; W-66 to K-720; L-67 to K-720; C-68 to K-720; V-69 to K-720; V-70 to K-720; P-71 to K-720; L-72 to K-720; F-73 to K-720; I-74 to K-720; G-75 to K-720; F-76 to K-720; I-77 to K-720; G-78 to K-720; L-79 to K-720; G-80 to K-720; L-81 to K-720; S-82 to K-720; L-83 to K-720; M-84 to K-720; L-85 to K-720; L-86 to K-720; K-87 to K-720; W-88 to K-720; I-89 to K-720; V-90 to K-720; V-91-to K-720; G-92 to K-720; S-93 to K-720; V-94 to K-720; K-95 to K-720; E-96 to K-720; Y-97 to K-720; V-98 to K-720; P-99 to K-720; T-100 to K-720; D-101 to K-720; L-102 to K-720; V-103 to K-720; D-104 to K-720; S-105 to K-720; K-106 to K-720; G-107 to K-720; M-108 to K-720; G-109 to K-720; Q-110 to K-720; D-111 to K-720; P-112 to K-720; F-113 to K-720; F-114 to K-720; L-115 to K-720; S-116 to K-720; K-117 to K-720; P-118 to K-720; S-119 to K-720; S-120 to K-720; F-121 to K-720; P-122 to K-720; K-123 to K-720; A-124 to K-720; M-125 to K-720; E-126 to K-720; T-127 to K-720; T-128 to K-720; T-129 to K-720; T-130 to K-720; T-131 to K-720; T-132 to K-720; S-133 to K-720; T-134 to K-720; T-135 to K-720; S-136 to K-720; P-137 to K-720; A-138 to K-720; T-139 to K-720; P-140 to K-720; S-141 to K-720; A-142 to K-720; G-143 to K-720; G-144 to K-720; A-145 to K-720; A-146 to K-720; S-147 to K-720; S-148 to K-720; R-149 to K-720; T-150 to K-720; P-151 to K-720; N-152 to K-720; R-153 to K-720; I-154 to K-720; S-155 to K-720; T-156 to K-720; T-157 to K-720; R-157 to K-720; L-158 to K-720; T-159 to K-720; T-160 to K-720; I-161 to K-720; T-162 to K-720; R-163 to K-720; A-164 to K-720; P-165 to K-720; T-166 to K-720; R-167 to K-720; F-168 to K-720; P-169 to K-720; G-170 to K-720; H-171 to K-720; R-172 to K-720; V-173 to K-720; P-174 to K-720; I-175 to K-720; R-176 to K-720; A-177 to K-720; S-178 to K-720; P-179 to K-720; R-180 to K-720; S-181 to K-720; T-182 to K-720; T-183 to K-720; A-184 to K-720; R-185 to K-720; N-186 to K-720; T-187 to K-720; A-188 to K-720; A-189 to K-720; P-190 to K-720; A-191 to K-720; T-192 to K-720; V-193 to K-720; P-194 to K-720; S-195 to K-720; T-196 to K-720; T-197 to K-720; A-198 to K-720; P-199 to K-720; F-200 to K-720; F-201 to K-720; S-202 to K-720; S-203 to K-720; S-204 to K-720; T-205 to K-720; L-206 to K-720; G-207 to K-720; S-208 to K-720; R-209 to K-720; P-210 to K-720; P-211 to K-720; V-212 to K-720; P-213 to K-720; G-214 to K-720; T-215 to K-720; P-216 to K-720; S-217 to K-720; T-218 to K-720; Q-219 to K-720; A-220 to K-720; M-221 to K-720; P-222 to K-720; S-223 to K-720, W-224 to K-720; P-225 to K-720; T-226 to K-720; A-227 to K-720; A-228 to K-720; Y-229 to K-720; A-230 to K-720; T-231 to K-720; S-232 to K-720; S-233 to K-720; Y-234 to K-720; L-235 to K-720; H-236 to K-720; D-237 to K-720; S-238 to K-720; T-239 to K-720; P-240 to K-720; S-241 to K-720; W-242 to K-720; T-243 to K-720; L-244 to K-720; S-245 to K-720; P-246 to K-720; F-247 to K-720; Q-248 to K-720; D-249 to K-720; A-250 to K-720; A-251 to K-720; S-252 to K-720; S-253 to K-720; S-254 to K-720; S-255 to K-720; S-256 to K-720; S-257 to K-720; S-258 to K-720; S-259 to K-720; S-260 to K-720; S-261 to K-720; T-262 to K-720; T-263 to K-720; T-264 to K-720; T-265 to K-720; P-266 to K-720; E-267 to K-720; T-268 to K-720; S-269 to K-720; T-270 to K-720; S-271 to K-720; P-272 to K-720; K-273 to K-720; F-274 to K-720; H-275 to K-720; T-276 to K-720; T-277 to K-720; T-278 to K-720; Y-279 to K-720; S-280 to K-720; T-281 to K-720; E-282 to K-720; R-283 to K-720; S-284 to K-720; E-285 to K-720; H-286 to K-720; F-287 to K-720; K-288 to K-720; P-289 to K-720; C-290 to K-720; R-291 to K-720; D-292 to K-720; K-293 to K-720; D-294 to K-720; L-295 to K-720; A-296 to K-720; Y-297 to K-720; C-298 to K-720; L-299 to K-720; N-300 to K-720; D-301 to K-720; G-302 to K-720; E-303 to K-720; C-304 to K-720; F-305 to K-720; V-306 to K-720; I-307 to K-720; E-308 to K-720; T-309 to K-720; L-310 to K-720; T-311 to K-720; G-312 to K-720, S-313 to K-720; H-314 to K-720; K-315 to K-720; H-316 to K-720; C-317 to K-720; R-318 to K-720; C-319 to K-720; K-320 to K-720; E-321 to K-720; G-322 to K-720; Y-323 to K-720; Q-324 to K-720; G-325 to K-720; V-326 to K-720; R-327 to K-720; C-328 to K-720; D-329 to K-720; Q-330 to K-720; F-331 to K-720; L-332 to K-720; P-333 to K-720; K-334 to K-720; T-335 to K-720; D-336 to K-720; S-337 to K-720; I-338 to K-720; L-339 to K-720; S-340 to K-720; D-341 to K-720; P-342 to K-720; T-343 to K-720; D-344 to K-720; H-345 to K-720; L-346 to K-720; G-347 to K-720; I-348 to K-720; E-349 to K-720; F-350 to K-720; M-351 to K-720; E-352 to K-720; S-353 to K-720; E-354 to K-720; E-355 to K-720; V-356 to K-720; Y-357 to K-720; Q-358 to K-720; R-359 to K-720; Q-360 to K-720; V-361 to K-720; L-362 to K-720; S-363 to K-720; I-364 to K-720; S-365 to K-720; C-366 to K-720; I-367 to K-720, I-368 to K-720; F-369 to K-720; G-370 to K-720; I-371 to K-720; V-372 to K-720; I-373 to K-720; V-374 to K-720; G-375 to K-720; M-376 to K-720; F-377 to K-720; C-378 to K-720; A-379 to K-720; A-380 to K-720; F-381 to K-720; Y-382 to K-720; F-383 to K-720; K-384 to K-720; S-385 to K-720; K-386 to K-720; K-387 to K-720; Q-388 to K-720; A-389 to K-720; K-390 to K-720; Q-391 to K-720; I-392 to K-720; Q-393 to K-720; E-394 to K-720; Q-395 to K-720; L-396 to K-720; K-397 to K-720; V-398 to K-720; P-399 to K-720; Q-400 to K-720; N-401 to K-720; G-402 to K-720; K-403 to K-720; S-404 to K-720; Y-405 to K-720; S-406 to K-720; L-407 to K-720; K-408 to K-720; A-409 to K-720; S-410 to K-720; S-411 to K-720; T-412 to K-720; M-413 to K-720; A-414 to K-720; K-415 to K-720; S-416 to K-720; E-417 to K-720; N-418 to K-720; L-419 to K-720; V-420 to K-720; K-421 to K-720; S-422 to K-720; H-423 to K-720; V-424 to K-720; Q-425 to K-720; L-426 to K-720; Q-427 to K-720; N-428 to K-720; Y-429 to K-720; S-430 to K-720; K-431 to K-720; V-432 to K-720; E-433 to K-720; R-434 to K-720; H-435 to K-720; P-436 to K-720; V-437 to K-720; T-438 to K-720; A-439 to K-720; L-440 to K-720; E-441 to K-720; K-442 to K-720; M-443 to K-720; M-444 to K-720; E-445 to K-720; S-446 to K-720; S-447 to K-720; F-448 to K-720; V-449 to K-720; G-450 to K-720; P-451 to K-720; Q-452 to K-720; S-453 to K-720; F-454 to K-720; P-455 to K-720; E-456 to K-720; V-457 to K-720; P-458 to K-720; S-459 to K-720; P-460 to K-720; D-461 to K-720; R-462 to K-720; G-463 to K-720; S-464 to K-720; Q-465 to K-720; S-466 to K-720;

V-467 to K-720; K-468 to K-720; H-469 to K-720; H-470 to K-720; R-471 to K-720; S-472 to K-720; L-473 to K-720; S-474 to K-720; S-475 to K-720; C-476 to K-720; C-477 to K-720; S-478 to K-720; P-479 to K-720; G-480 to K-720; Q-481 to K-720; R-482 to K-720; S-483 to K-720; G-484 to K-720; M-485 to K-720; L-486 to K-720; H-487 to K-720; R-488 to K-720; N-489 to K-720; A-490 to K-720; F-491 to K-720; R-492 to K-720; R-493 to K-720; T-494 to K-720; P-495 to K-720; P-496 to K-720; S-497 to K-720; P-498 to K-720; R-499 to K-720; S-500 to K-720; R-501 to K-720; L-502 to K-720; G-503 to K-720; G-504 to K-720; I-505 to K-720; V-506 to K-720; G-507 to K-720; P-508 to K-720; A-509 to K-720; Y-510 to K-720; Q-511 to K-720; Q-512 to K-720; L-513 to K-720; E-514 to K-720; E-515 to K-720; S-516 to K-720; R-517 to K-720; I-518 to K-720; P-519 to K-720; D-520 to K-720; Q-521 to K-720; D-522 to K-720; T-523 to K-720; I-524 to K-720; P-525 to K-720; C-526 to K-720; Q-527 to K-720; G-528 to K-720; I-529 to K-720; E-530 to K-720; V-531 to K-720; R-532 to K-720; K-533 to K-720; T-534 to K-720; I-535 to K-720; S-536 to K-720; H-537 to K-720; L-538 to K-720; P-539 to K-720; I-540 to K-720; Q-541 to K-720; L-542 to K-720; W-543 to K-720; C-544 to K-720; V-545 to K-720; E-546 to K-720; R-547 to K-720; P-548 to K-720; L-549 to K-720; D-550 to K-720; L-551 to K-720; K-552 to K-720; Y-553 to K-720; S-554 to K-720; S-555 to K-720; S-556 to K-720; G-557 to K-720; L-558 to K-720; K-559 to K-720; T-560 to K-720; Q-561 to K-720; R-562 to K-720; N-563 to K-720; T-564 to K-720; S-565 to K-720; I-566 to K-720; N-567 to K-720; M-568 to K-720; Q-569 to K-720; L-570 to K-720; P-571 to K-720; S-572 to K-720; R-573 to K-720; E-574 to K-720; T-575 to K-720; N-576 to K-720; P-577 to K-720; Y-578 to K-720; F-579 to K-720; N-580 to K-720; S-581 to K-720; L-582 to K-720; E-583 to K-720; Q-584 to K-720; K-585 to K-720; D-586 to K-720; L-587 to K-720; V-588 to K-720; G-589 to K-720; Y-590 to K-720; S-591 to K-720; S-592 to K-720; T-593 to K-720; R-594 to K-720; A-595 to K-720; S-596 to K-720; S-597 to K-720; V-598 to K-720; P-599 to K-720; I-600 to K-720; I-601 to K-720; P-602 to K-720; S-603 to K-720; V-604 to K-720; G-605 to K-720; L-606 to K-720; E-607 to K-720; E-608 to K-720; T-609 to K-720; C-610 to K-720; L-611 to K-720; Q-612 to K-720; M-613 to K-720; P-614 to K-720; G-615 to K-720; L-616 to K-720; S-617 to K-720; E-618 to K-720; V-619 to K-720; K-620 to K-720; S-621 to K-720; I-622 to K-720; K-623 to K-720; W-624 to K-720, C-625 to K-720; K-626 to K-720; N-627 to K-720; S-628 to K-720; Y-629 to K-720; S-630 to K-720; A-631 to K-720; D-632 to K-720; V-633 to K-720; V-634 to K-720; N-635 to K-720; V-636 to K-720; S-637 to K-720; I-638 to K-720; P-639 to K-720; V-640 to K-720; S-641 to K-720; D-642 to K-720; C-643 to K-720; L-644 to K-720; I-645 to K-720; A-646 to K-720; E-647 to K-720; Q-648 to K-720; Q-649 to K-720; E-650 to K-720; V-651 to K-720; K-652 to K-720; I-653 to K-720; L-654 to K-720; L-655 to K-720; E-656 to K-720; T-657 to K-720; V-658 to K-720; Q-659 to K-720; E-660 to K-720; Q-661 to K-720; I-662 to K-720; R-663 to K-720; I-664 to K-720; L-665 to K-720; T-666 to K-720; D-667 to K-720; A-668 to K-720; R-669 to K-720; R-670 to K-720; S-671 to K-720; E-672 to K-720; D-673 to K-720; Y-674 to K-720; E-675 to K-720; L-676 to K-720; A-677 to K-720; S-678 to K-720; V-679 to K-720; E-680 to K-720; T-681 to K-720; E-682 to K-720; D-683 to K-720; S-684 to K-720; A-685 to K-720; S-686 to K-720; E-687 to K-720; N-688 to K-720; T-689 to K-720; A-690 to K-720; F-691 to K-720; L-692 to K-720; P-693 to K-720; L-694 to K-720; S-695 to K-720; P-696 to K-720; T-697 to K-720; A-698 to K-720; K-699 to K-720; S-700 to K-720; E-701 to K-720; R-702 to K-720; E-703 to K-720; A-704 to K-720; Q-705 to K-720; F-706 to K-720; V-707 to K-720; L-708 to K-720; R-709 to K-720; N-710 to K-720; E-711 to K-720; I-712 to K-720; Q-713 to K-720; R-714 to K-720; and D-715 to K-720 of the HLF sequence shown in SEQ ID NO:22. Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened HLF mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that an HLF mutein with a large number of deleted C-terminal amino acid residues may retain some biological or immunogenic activities. In fact, peptides composed of as few as six HLF amino acid residues may often evoke an immune response.

Accordingly, the present invention further provides polypeptides having one or more residues deleted from the carboxy terminus of the amino acid sequence of the HLF shown in SEQ ID NO:22, up to the alanine residue at position number 6, and polynucleotides encoding such polypeptides. In particular, the present invention provides polypeptides comprising the amino acid sequence of residues 1-m" of SEQ ID NO:22, where m" is an integer in the range of 7–718, and 6 is the position of the first residue from the C-terminus of the complete HLF polypeptide believed to be required for at least immunogenic activity of the HLF protein.

More in particular, the invention provides polynucleotides encoding polypeptides comprising, or alternatively consisting of, the amino acid sequence of residues M-1 to T-719; M-1 to L-718; M-1 to A-717; M-1 to S-716; M-1 to D-715; M-1 to R-714; M-1 to Q-713; M-1 to I-712; M-1 to E-711; M-1 to N-710; M-1 to R-709; M-1 to L-708; M-1 to V-707; M-1 to F-706; M-1 to Q-705; M-1 to A-704; M-1 to E-703; M-1 to R-702; M-1 to E-701; M-1 to S-700; M-1 to K-699; M-1 to A-698; M-1 to T-697; M-1 to P-696; M-1 to S-695; M-1 to L-694; M-1 to P-693; M-1 to L-692; M-1 to F-691; M-1 to A-690; M-1 to T-689; M-1 to N-688; M-1 to E-687; M-1 to S-686; M-1 to A-685; M-1 to S-684; M-1 to D-683; M-1 to E-682; M-1 to T-681; M-1 to E-680; M-1 to V-679; M-1 to S-678; M-1 to A-677; M-1 to L-676; M-1 to E-675; M-1 to Y-674; M-1 to D-673; M-1 to E-672; M-1 to S-671; M-1 to R-670; M-1 to R-669; M-1 to A-668; M-1 to D-667; M-1 to T-666; M-1 to L-665; M-1 to I-664; M-1 to R-663; M-1 to I-662; M-1 to Q-661; M-1 to E-660; M-1 to Q-659; M-1 to V-658; M-1 to T-657; M-1 to E-656; M-1 to L-655; M-1 to L-654; M-1 to I-653; M-1 to K-652; M-1 to V-651; M-1 to E-650; M-1 to Q-649; M-1 to Q-648; M-1 to E-647; M-1 to A-646; M-1 to I-645; M-1 to L-644, M-1 to C-643; M-1 to D-642; M-1 to S-641; M-1 to V-640; M-1 to P-639; M-1 to I-638; M-1 to S-637; M-1 to V-636; M-1 to N-635; M-1 to V-634; M-1 to V-633; M-1 to D-632; M-1 to A-631; M-1 to S-630; M-1 to Y-629; M-1 to S-628; M-1 to N-627; M-1 to K-626; M-1 to C-625; M-1 to W-624; M-1 to K-623; M-1 to I-622; M-1 to S-621; M-1 to K-620; M-1 to V-619; M-1 to E-618; M-1 to S-617; M-1 to I-616; M-1 to G-615; M-1 to P-614; M-1 to M-613; M-1 to Q-612; M-1 to L-611; M-1 to C-610; M-1 to T-609; M-1 to E-608; M-1 to E-607;

M-1 to L-606; M-1 to G-605; M-1 to V-604; M-1 to S-603; M-1 to P-602; M-1 to I-601; M-1 to I-600; M-1 to P-599; M-1 to V-598; M-1 to S-597; M-1 to S-596; M-1 to A-595; M-1 to R-594; M-1 to T-593; M-1 to S-592; M-1 to S-591; M-1 to Y-590; M-1 to G-589; M-1 to V-588; M-1 to L-587; M-1 to D-586; M-1 to K-585; M-1 to Q-584; M-1 to E-583; M-1 to L-582; M-1 to S-581; M-1 to N-580; M-1 to F-579; M-1 to Y-578; M-1 to P-577; M-1 to N-576; M-1 to T-575; M-1 to E-574; M-1 to R-573; M-1 to S-572; M-1 to P-571; M-1 to L-570; M-1 to Q-569; M-1 to M-568; M-1 to N-567; M-1 to I-566; M-1 to S-565; M-1 to T-564; M-1 to N-563; M-1 to R-562; M-1 to Q-561; M-1 to T-560; M-1 to K-559; M-1 to L-558; M-1 to G-557; M-1 to S-556; M-1 to S-555; M-1 to S-554; M-1 to Y-553; M-1 to K-552; M-1 to L-551; M-1 to D-550; M-1 to L-549; M-1 to P-548; M-1 to R-547; M-1 to E-546; M-1 to V-545; M-1 to C-544; M-1 to W-543; M-1 to L-542; M-1 to Q-541; M-1 to I-540; M-1 to P-539; M-1 to L-538; M-1 to H-537; M-1 to S-536; M-1 to I-535; M-1 to T-534; M-1 to K-533; M-1 to R-532; M-1 to V-531; M-1 to E-530; M-1 to I-529; M-1 to G-528; M-1 to Q-527; M-1 to C-526; M-1 to P-525; M-1 to I-524; M-1 to T-523; M-1 to D-522; M-1 to Q-521; M-1 to D-520; M-1 to P-519; M-1 to I-518; M-1 to R-517; M-1 to S-516; M-1 to E-515; M-1 to E-514; M-1 to L-513; M-1 to Q-512; M-1 to Q-511; M-1 to Y-510; M-1 to A-509; M-1 to P-508; M-1 to G-507; M-1 to V-506; M-1 to I-505; M-1 to G-504; M-1 to G-503; M-1 to L-502; M-1 to R-501; M-1 to S-500; M-1 to R-499; M-1 to P-498; M-1 to S-497; M-1 to P-496; M-1 to P-495; M-1 to T-494; M-1 to R-493; M-1 to R-492; M-1 to F-491; M-1 to A-490; M-1 to N-489; M-1 to R-488; M-1 to H-487; M-1 to L-486; M-1 to M-485; M-1 to G-484; M-1 to S-483; M-1 to R-482; M-1 to Q-481; M-1 to G-480; M-1 to P-479; M-1 to S-478; M-1 to C-477; M-1 to C-476; M-1 to S-475; M-1 to S-474; M-1 to L-473; M-1 to S-472; M-1 to R-471; M-1 to H-470; M-1 to H-469; M-1 to K-468; M-1 to V-467; M-1 to S-466; M-1 to Q-465; M-1 to S-464; M-1 to G-463; M-1 to R-462; M-1 to D-461; M-1 to P-460; M-1 to S-459; M-1 to P-458; M-1 to V-457; M-1 to E-456; M-1 to P-455; M-1 to F-454; M-1 to S-453; M-1 to Q-452; M-1 to P-451; M-1 to G-450; M-1 to V-449; M-1 to F-448; M-1 to S-447; M-1 to S-446; M-1 to E-445; M-1 to M-444; M-1 to M-443; M-1 to K-442; M-1 to E-441; M-1 to L-440; M-1 to A-439; M-1 to T-438; M-1 to V-437; M-1 to P-436; M-1 to H-435; M-1 to R-434; M-1 to R-433; M-1 to V-432; M-1 to K-431; M-1 to S-430; M-1 to Y-429; M-1 to N-428; M-1 to Q-427; M-1 to L-426; M-1 to Q-425; M-1 to V-424; M-1 to H-423; M-1 to S-422; M-1 to K-421; M-1 to V-420; M-1 to L-419; M-1 to N-418; M-1 to E-417; M-1 to S-416; M-1 to K-415; M-1 to A-414; M-1 to M-413; M-1 to T-412; M-1 to S-411; M-1 to S-410; M-1 to A-409; M-1 to K-408; M-1 to L-407; M-1 to S-406; M-1 to Y-405; M-1 to S-404; M-1 to K-403; M-1 to G-402; M-1 to N-401; M-1 to Q-400; M-1 to P-399; M-1 to V-398; M-1 to K-397; M-1 to L-396; M-1 to Q-395; M-1 to E-394; M-1 to Q-393; M-1 to I-392; M-1 to Q-391; M-1 to K-390; M-1 to A-389; M-1 to Q-388; M-1 to K-387; M-1 to K-386; M-1 to S-385; M-1 to K-384; M-1 to F-383; M-1 to Y-382; M-1 to F-381; M-1 to A-380; M-1 to A-379; M-1 to C-378; M-1 to F-377; M-1 to M-376; M-1 to G-375; M-1 to V-374; M-1 to I-373; M-1 to V-372; M-1 to I-371; M-1 to G-370; M-1 to F-369; M-1 to I-368; M-1 to I-367; M-1 to C-366; M-1 to S-365; M-1 to I-364; M-1 to S-363; M-1 to L-362; M-1 to V-361; M-1 to Q-360; M-1 to R-359; M-1 to Q-358; M-1 to Y-357; M-1 to V-356; M-1 to E-355; M-1 to E-354; M-1 to S-353; M-1 to E-352; M-1 to M-351; M-1 to F-350; M-1 to E-349; M-1 to I-348; M-1 to G-347; M-1 to L-346; M-1 to H-345; M-1 to D-344; M-1 to T-343; M-1 to P-342; M-1 to D-341; M-1 to S-340; M-1 to L-339; M-1 to I-338; M-1 to S-337; M-1 to D-336; M-1 to T-335; M-1 to K-334; M-1 to P-333; M-1 to L-332; M-1 to F-331; M-1 to Q-330; M-1 to D-329; M-1 to C-328; M-1 to R-327; M-1 to V-326; M-1 to G-325; M-1 to Q-324; M-1 to Y-323; M-1 to G-322; M-1 to E-321; M-1 to K-320; M-1 to C-319; M-1 to R-318; M-1 to C-317; M-1 to H-316; M-1 to K-315; M-1 to H-314; M-1 to S-313; M-1 to G-312; M-1 to T-311; M-1 to L-310; M-1 to T-309; M-1 to E-308; M-1 to I-307; M-1 to V-306; M-1 to F-305; M-1 to C-304; M-1 to E-303; M-1 to G-302; M-1 to D-301; M-1 to N-300; M-1 to L-299; M-1 to C-298; M-1 to Y-297; M-1 to A-296; M-1 to L-295; M-1 to D-294; M-1 to K-293; M-1 to D-292; M-1 to R-291; M-1 to C-290; M-1 to P-289; M-1 to K-288; M-1 to F-287; M-1 to H-286; M-1 to E-285; M-1 to S-284; M-1 to R-283; M-1 to E-282; M-1 to T-281; M-1 to S-280; M-1 to Y-279; M-1 to T-278; M-1 to T-277; M-1 to T-276; M-1 to H-275; M-1 to F-274; M-1 to K-273; M-1 to P-272; M-1 to S-271; M-1 to T-270; M-1 to S-269; M-1 to T-268; M-1 to E-267; M-1 to P-266; M-1 to T-265; M-1 to T-264; M-1 to T-263; M-1 to T-262; M-1 to S-261; M-1 to S-260; M-1 to S-259; M-1 to S-258; M-1 to S-257; M-1 to S-256; M-1 to S-255; M-1 to S-254; M-1 to S-253; M-1 to S-252; M-1 to A-251; M-1 to A-250; M-1 to D-249; M-1 to Q-248; M-1 to F-247; M-1 to P-246; M-1 to S-245; M-1 to L-244; M-1 to T-243; M-1 to W-242; M-1 to S-241; M-1 to P-240; M-1 to T-239; M-1 to S-238; M-1 to D-237; M-1 to H-236; M-1 to L-235; M-1 to Y-234; M-1 to S-233; M-1 to S-232; M-1 to T-231; M-1 to A-230; M-1 to Y-229; M-1 to A-228; M-1 to A-227; M-1 to T-226; M-1 to P-225; M-1 to W-224; M-1 to S-223; M-1 to P-222; M-1 to M-221; M-1 to A-220; M-1 to Q-219; M-1 to T-218; M-1 to S-217; M-1 to P-216; M-1 to T-215; M-1 to G-214; M-1 to P-213; M-1 to V-212; M-1 to P-211; M-1 to P-210; M-1 to R-209; M-1 to S-208; M-1 to G-207; M-1 to L-206; M-1 to T-205; M-1 to S-204; M-1 to S-203; M-1 to S-202; M-1 to F-201; M-1 to F-200; M-1 to P-199; M-1 to A-198; M-1 to T-197; M-1 to T-196; M-1 to S-195; M-1 to P-194; M-1 to V-193; M-1 to T-192; M-1 to A-191; M-1 to P-190; M-1 to A-189; M-1 to A-188; M-1 to T-187; M-1 to N-186; M-1 to R-185; M-1 to A-184; M-1 to T-183; M-1 to T-182; M-1 to S-181; M-1 to R-180; M-1 to P-179; M-1 to S-178; M-1 to A-177; M-1 to R-176; M-1 to I-175; M-1 to P-174; M-1 to V-173; M-1 to R-172; M-1 to H-171; M-1 to G-170; M-1 to P-169; M-1 to F-168; M-1 to R-167; M-1 to T-166; M-1 to P-165; M-1 to A-164; M-1 to R-163; M-1 to T-162; M-1 to I-161; M-1 to T-160; M-1 to T-159; M-1 to L-158; M-1 to R-157; M-1 to T-156; M-1 to S-155; M-1 to I-154; M-1 to R-153; M-1 to N-152; M-1 to P-151; M-1 to T-150; M-1 to R-149; M-1 to S-148; M-1 to S-147; M-1 to A-146; M-1 to A-145; M-1 to G-144; M-1 to G-143; M-1 to A-142; M-1 to S-141; M-1 to P-140; M-1 to T-139; M-1 to A-138; M-1 to P-137; M-1 to S-136; M-1 to T-135; M-1 to T-134; M-1 to S-133; M-1 to T-132; M-1 to T-131; M-1 to T-130; M-1 to T-129; M-1 to T-128; M-1 to T-127; M-1 to E-126; M-1 to M-125; M-1 to A-124; M-1 to K-123; M-1 to P-122; M-1 to F-121; M-1 to S-120; M-1 to S-119; M-1 to P-118; M-1 to K-117; M-1 to S-116; M-1 to L-115; M-1 to F-114; M-1 to F-113; M-1 to P-112; M-1 to D-111; M-1 to Q-110; M-1 to G-109; M-1 to M-108; M-1 to G-107; M-1 to K-106; M-1 to S-105; M-1 to D-104; M-1 to V-103; M-1 to L-102; M-1 to D-101; M-1 to T-100; M-1 to P-99; M-1 to V-98; M-1 to Y-97; M-1 to E-96; M-1 to K-95; M-1 to V-94; M-1 to S-93; M-1 to G-92; M-1 to V-91; M-1 to V-90; M-1 to I-89; M-1 to W-88; M-1 to K-87; M-1 to L-86; M-1 to L-85; M-1 to M-84; M-1 to L-83; M-1 to S-82; M-1 to L-81; M-1 to G-80; M-1 to L-79; M-1 to G-78; M-1 to I-77; M-1 to F-76; M-1 to G-75; M-1 to I-74; M-1 to F-73; M-1 to L-72; M-1 to P-71; M-1 to V-70; M-1 to V-69; M-1 to C-68; M-1 to L-67; M-1 to W-66; M-1 to T-65; M-1 to Q-64; M-1 to Q-63; M-1 to R-62; M-1 to N-61; M-1 to W-60; M-1 to V-59; M-1 to I-58; M-1 to C-57; M-1 to D-56; M-1 to S-55; M-1 to C-54; M-1 to R-53; M-1 to L-52; M-1 to E-51; M-1 to R-50; M-1 to P-49; M-1 to P-48; M-1 to E-47; M-1 to A-46; M-1 to A-45; M-1 to G-44; M-1 to E-43; M-1 to G-42; M-1 to G-41; M-1 to G-40; M-1 to D-39; M-1 to P-38; M-1 to G-37; M-1 to G-36; M-1 to G-35; M-1 to A-34; M-1 to A-33; M-1 to A-32; M-1 to A-31; M-1 to A-30; M-1 to A-29; M-1 to A-28; M-1 to A-27; M-1 to A-26; M-1 to T-25; M-1 to G-24; M-1 to E-23; M-1 to E-22; M-1 to A-21; M-1 to S-20; M-1 to A-19; M-1 to A-18; M-1 to A-17; M-1 to A-16; M-1 to S-15; M-1 to A-14; M-1 to A-13; M-1 to G-12; M-1 to P-11; M-1 to P-10; M-1 to S-9; M-1 to A-8; M-1 to A-7; M-1 to A-6 of the HLF sequence shown in SEQ ID NO:22. Polynucleotides encoding these polypeptides also are provided.

The invention also provides polypeptides having one or more amino acids deleted from both the amino and the carboxyl termini of an HLF polypeptide, which may be described generally as having residues n"-m" of SEQ ID NO:22, where n" and m" are integers as described above.

Other Mutants

In addition to terminal deletion forms of the protein discussed above, it also will be recognized by one of ordinary skill in the art that some amino acid sequences of the HLF polypeptide can be varied without significant effect of the structure or function of the protein. If such differences in sequence are contemplated, it should be remembered that there will be critical areas on the protein which determine activity.

Thus, the invention further includes variations of the HLF polypeptide which show substantial HLF polypeptide activity or which include regions of HLF protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided by Bowie and colleagues (*Science* 247:1306–1310; 1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the extracellular domain of the HLF polypeptide is fused with another compound, such as a compound to increase the half-life of the polypeptide (for example, polyethylene glycol), (iv) one in which the EGF domain of the HLF polypeptide is fused with another compound, such as a compound to increase the half-life of the polypeptide (for example, polyethylene glycol), (v) one in which the additional amino acids are fused to the extracellular form of the polypeptide, such as an IgG Fc fusion region peptide or leader or secretory sequence or a sequence which is employed for purification of the above form of the polypeptide or a proprotein sequence, or (vi) one in which the additional amino acids are fused to the EGF form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the HLF of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, deletions or additions in the amino acid sequence of FIG. 1A and/or any of the polypeptide fragments described herein is 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or 30-20, 20-10, 20-15, 15-10, 10-5 or 1-5.

Amino acids in the HLF protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Since HLF is a member of the EGF-related protein family, to modulate rather than completely eliminate biological activities of HLF, preferably mutations are made in sequences encoding amino acids in the HLF conserved domain, i.e., in amino acid positions about 26 to about 93 of SEQ ID NO:2, more preferably in residues within this region which are not conserved in all members of the EGF family. Also forming part of the present invention are isolated polynucleotides comprising nucleic acid sequences which encode the above HLF mutants.

The polypeptides of the present invention are preferably provided in an isolated form, and preferably are substantially purified. A recombinantly produced version of the HLF polypeptide can be substantially purified by the one-step method described by Smith and Johnson (*Gene* 67:31–40; 1988). Polypeptides of the invention also can be purified from natural or recombinant sources using anti-HLF antibodies of the invention in methods which are well known in the art of protein purification.

The invention further provides an isolated HLF polypeptide comprising an amino acid sequence selected from the group consisting of: (a) the amino acid sequence of the HLF polypeptide having the complete amino acid sequence shown in SEQ ID NO:2 (i.e., positions 1 to 157 of SEQ ID NO:2) or the complete amino acid sequence encoded by the cDNA clone contained in the ATCC Deposit No. 209123; (b) the amino acid sequence of the predicted extracellular domain of the HLF polypeptide having the amino acid sequence shown in SEQ ID NO:2 (i.e., positions 1 to 101 of SEQ ID NO:2) or as encoded by the cDNA clone contained in the ATCC Deposit No. 209123; (c) the amino acid sequence of the predicted transmembrane domain of the HLF polypeptide having the amino acid sequence shown in SEQ ID NO:2 (i.e., positions 102 to 121 of SEQ ID NO:2) or as encoded by the cDNA clone contained in the ATCC Deposit No. 209123; (d) the amino acid sequence of the predicted intracellular domain of the HLF polypeptide having the amino acid sequence shown in SEQ ID NO:2 (i.e., positions 122 to 157 of SEQ ID NO:2) or as encoded by the cDNA clone contained in the ATCC Deposit No. 209123; and (e) the amino acid sequence of a soluble HLF polypeptide having the extracellular and intracellular domains but lacking the transmembrane domain. The polypeptides of the present invention also include polypeptides having an amino acid sequence at least 80% identical, more preferably at least 90% identical, and still more preferably 95%, 96%, 97%, 98% or 99% identical to (or at most 20% different, more preferably at most 10% different, and still more preferably 5%, 4%, 3%, 2% or 1% different from) those described in (a), (b), (c), (d), or (e) above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to (or at most 20% different, more preferably at most 10% or 5% different, still more preferably at most 4%, 3%, 2% or 1% different from) the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Adv. Appl. Math.* 2:482–489; 1981) to find the best segment of similarity between two sequences.

By a polypeptide having an amino acid sequence at least, for example, 95% "identical" to a reference amino acid sequence of an HLF polypeptide is intended that the amino acid sequence of the polypeptide is identical to the reference sequence except that the polypeptide sequence may include up to five amino acid alterations per each 100 amino acids of the reference amino acid of the HLF polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to (or at most 10%, 5%, 4%, 3%, 2% or 1% different from), for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to (or 5% different from) a reference sequence according to the present invention, the parameters are set, of course, such that the percentage of identity is calculated over the full length of the reference amino acid sequence and that gaps in homology of up to 5% of the total number of amino acid residues in the reference sequence are allowed.

By a polypeptide having an amino acid sequence at least, for example, 95% "identical" to (or 5% different from) a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to (or at most 10%, 5%, 4%, 3%, 2% or 1% different from) for instance, the amino acid sequences shown in SEQ ID NO:2 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting HLF protein expression as described below or as agonists and antagonists capable of enhancing or inhibiting HLF protein function. Further, such polypeptides can be used in the yeast two-hybrid system to "capture" HLF protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (Geysen et al., *Proc. Natl. Acad. Sci. USA* 81:3998–4002; 1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (Sutcliffe, J. G., et al., *Science* 219:660–666; 1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate HLF-specific antibodies include: a polypeptide comprising amino acid residues from about Ser-1 to about Thr-8, about Thr-9 to about Lys-18, about Thr-23 to about His-31, about Phe-32 to about Leu-40, about Cys-43 to about Val-51, about Thr-56 to about Tyr-68, about Gln-75 to about Leu-84, about Tyr-126 to about Ala-135, about Ser-137 to about Leu-146, and about Ser-148 to about Lys-157. These polypeptide fragments have been determined to bear antigenic epitopes of the HLF protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, HLF polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86; 1988). Fusion proteins that have a disulfide-linked dimeric structure due to the IgG part can also be more efficient in binding and neutralizing other molecules than the monomeric HLF protein or protein fragment alone (Fountoulakis, et al., *J. Biochem.* 270:3958–3964; 1995).

Furthermore, HLF polypeptides of interest of the present invention, for example the extracellular EGF-like domain shown in FIG. 1A, can be combined with a recombinant toxin. Such a fusion polypeptide can be used to target the toxin, for example *Pseudomonas* exotoxin A, to a tumor through the efficient binding of the extracellular or smaller soluble domains of the HLF molecule of the present invention. In fact, Jeschke and colleagues (*Int. J. Cancer* 60:730–739; 1995) and Fiddes and coworkers (*Cell Growth Differ.* 6:1567–1577; 1995) have demonstrated that heregulin-toxin fusion proteins can be utilized in such a fashion.

Antibodies

HLF-protein specific antibodies for use in the present invention can be raised against the intact HLF protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to HLF protein. Fab and F(ab)2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the HLF protein or an antigenic fragment thereof can be administered to an animal in order to induce the production of sera containing polyclonal antibodies. In a preferred method, a preparation of HLF protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or HLF protein binding fragments thereof). Such monoclonal antibodies can be prepared using hybridoma technology (Kohler et al., *Nature* 256:495 (1975); Köhler et al., *Eur. J. Immunol.* 6:511 (1976); Kohler et al., Eur. J. Immunol. 6:292 (1976); Hammerling et al., in: *Monoclonal Antibodies and T-Cell Hybridomas,* Elsevier, N.Y., (1981) pp. 563–681). In general, such procedures involve immunizing an animal (preferably a mouse) with a HLF protein antigen or, more preferably, with a HLF protein-expressing cell. Suitable cells can be recognized by their capacity to bind anti-HLF protein antibody. Such cells may be cultured in any suitable tissue culture medium; however, it is preferable to culture cells in Earle's modified Eagle's medium supplemented with 10% fetal bovine serum (inactivated) at about 56° C.), and supplemented with about 10 g/l of nonessential amino, acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the HLF protein antigen.

Alternatively, additional antibodies capable of binding to the HLF protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, HLF-protein specific antibodies are used to immunize an animal, preferably a mouse. The splenocytes of such an animal are then used to produce hybridoma cells, and the hybridoma cells are screened to identify clones which produce an antibody whose ability to bind to the HLF protein-specific antibody can be blocked by the HLF protein antigen. Such antibodies comprise anti-idiotypic antibodies to the HLF protein-specific antibody and can be used to immunize an animal to induce formation of further HLF protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, HLF protein-binding fragments can be produced through the application of recombinant DNA technology or through synthetic chemistry.

For in vivo use of anti-HLF in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, Science 229:1202; 1985); Oi, et al., BioTechniques 4:214; 1986; Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., Nature 312:643; 1984; Neuberger et al., Nature 314:268; 1985).

Disorders Related to the Regulation of Cell Growth

Diagnosis

The present inventors have discovered that HLF is apparently expressed detectably only in the amygdala, whole brain, and primary breast culture tissue. For a number of disorders related to the regulation of cell growth, substantially altered (increased or decreased) levels of HLF gene expression can be detected in tissues or other cells or bodily fluids (e.g., sera, plasma, urine, synovial fluid or spinal fluid) taken from an individual having such a disorder, relative to a "standard" HLF gene expression level, that is, the HLF expression level in such tissues or bodily fluids from an individual not having the disorder. Thus, the invention provides a diagnostic method useful during diagnosis of a disorder related to the regulation of cell growth, which involves measuring the expression level of the gene encoding the HLF protein in such tissues or other cells or bodily fluids from an individual and comparing the measured gene expression level with a standard HLF gene expression level, whereby an increase or decrease in the gene expression level compared to the standard is indicative of a such a disorder.

In particular, it is believed that certain tissues in mammals with breast or brain cancers express significantly enhanced levels of the HLF protein and mRNA encoding the HLF protein when compared to a corresponding "standard" level. Further, it is believed that enhanced levels of the HLF protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of a disorder of the regulation of cell growth, including several types of cancers which involves measuring the expression level of the gene encoding the HLF protein in tissues or other cells or bodily fluids from an individual and comparing the measured gene expression level with a standard HLF gene expression level, whereby an increase or decrease in the gene expression level compared to the standard is indicative of such a disorder.

Where a diagnosis of a disorder of the regulation of cell growth, including diagnosis of a tumor, has already been made according to conventional methods, the present invention is useful as a prognostic indicator, whereby patients exhibiting enhanced HLF gene expression will experience a worse clinical outcome relative to patients expressing the gene at a level nearer the standard level.

By "assaying the expression level of the gene encoding the HLF protein" is intended qualitatively or quantitatively measuring or estimating the level of the HLF protein or the level of the mRNA encoding the HLF protein in a first biological sample either directly (e.g., by determining or estimating absolute protein level or mRNA level) or relatively (e.g., by comparing to the HLF protein level or mRNA level in a second biological sample). Preferably, the HLF protein level or mRNA level in the first biological sample is measured or estimated and compared to a standard HLF protein level or mRNA level, the standard being taken from a second biological sample obtained from an individual not having the disorder or being determined by averaging levels from a population of individuals not having a disorder of the regulation of cell growth. As will be appreciated in the art, once a standard HLF protein level or mRNA level is known, it can be used repeatedly as a standard for comparison.

By "biological sample" is intended any biological sample obtained from an individual, body fluid, cell line, tissue culture, or other source which contains HLF protein or mRNA. As indicated, biological samples include body fluids (such as sera, plasma, urine, synovial fluid and spinal fluid) which contain free HLF protein, or the extracellular or EGF domains of the HLF protein, cancerous tissue, and other tissue sources found to express complete HLF protein, or the extracellular or EGF domains of the HLF protein, or an HLF receptor. Methods for obtaining tissue biopsies and body fluids from mammals are well known in the art. Where the biological sample is to include mRNA, a tissue biopsy is the preferred source.

The present invention is useful for diagnosis or treatment of various disorders of the regulation of cell growth in mammals, preferably humans. Such disorders include breast cancer, brain cancers, including neuroblastomas and glioblastomas, developmental disorders, ovarian cancer, endometrial cancer, some types of colon cancers, and the like.

Total cellular RNA can be isolated from a biological sample using any suitable technique such as the single-step guanidinium-thiocyanate-phenol-chloroform method described by Chomczynski and Sacchi (*Anal. Biochem.* 162:156–159; 1987). Levels of mRNA encoding the HLF protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying HLF protein levels in a biological sample can occur using antibody-based techniques. For example, HLF protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting HLF protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying HLF protein levels in a biological sample obtained from an individual, HLF protein can also be detected in vivo by imaging. Antibody labels or markers for in vivo imaging of HLF protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A HLF protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain HLF protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, HLF polynucleotides and polypeptides are useful for diagnosis of conditions involving abnormally high or low expression of HLF activities. Given the cells and tissues where HLF is expressed as well as the activities modulated by HLF, it is readily apparent that a substantially altered (increased or decreased) level of expression of HLF in an individual compared to the standard or "normal" level produces pathological conditions related to the bodily system(s) in which HLF is expressed and/or is active.

It will also be appreciated by one of ordinary skill that, since the HLF protein of the invention is a member of the EGF family the extracellular domain of the protein may be released in soluble form from the cells which express the HLF by proteolytic cleavage. Therefore, when HLF soluble extracellular domain is added from an exogenous source to cells, tissues or the body of an individual, the protein will exert its physiological activities on its target cells of that individual.

Therefore, it will be appreciated that conditions caused by a decrease in the standard or normal level of HLF activity in an individual, particularly disorders of cellular growth regulation, can be treated by administration of HLF polypeptide (in the form of soluble extracellular domain or cells expressing the complete protein. Thus, the invention also provides a method of treatment of an individual in need of an increased level of HLF activity comprising administering to such an individual a pharmaceutical composition comprising an amount of an isolated HLF polypeptide of the invention, particularly an extracellular form of the HLF protein of the invention, effective to increase the HLF activity level in such an individual.

An individual who is in need of increased HLF activity will not express a sufficient amount of functional HLF protein, administration of recombinant HLF protein, or more simply, of the active extracellular or the active EGF domain, to such an individual will result in the presence of a sufficient concentration of HLF activity in the bloodstream. In addition, an individual who has an abnormally increased level of HLF activity, will require the use of an HLF antibody or antagonist, as described in the present invention. The use of such HLF antagonists will result in a therapeutic lowering of the effective level of HLF activity in the bloodstream. As a result of such treatment, the affected individual will have an effective concentration of HLF activity which is much closer to that of what is deemed "normal". Those of skill in the art will recognize other indications where the ability to therapeutically adjust the level of effective HLF activity is desirable.

It will be further appreciated by one of ordinary skill that HLF may be used as an additive or supplement for the in vitro culture of certain types of eukaryotic cells. Many cell types, including primary cell cultures, are highly fastidious and require a complex mixture of additives to the standard culture medium to result in successful culture and survival of the cells. A number of known growth factors and related molecules are currently used as supplements to the medium of various cells. Such factors may include molecules as epidermal growth factor (EGF), keratinocyte growth factor (KGF), acidic fibroblast growth factor (aFGF), insulin-like growth factor (IGF)-I, nerve growth factor (NGF), and many others. Despite the availability and use of the collection of growth factors listed above, a large number of cells and cell types remain unculturable, either at all or for an extended period of time. Since expression of HLF appears to be limited to the amygdala, whole brain, and primary breast culture tissue or to other neural cells and tissues, HLF is useful as an additive or growth factor in the culture of neural and a number of other cells and cell types.

It will be further appreciated by the skilled artisan, that many cells and cell types require the absence of a specific growth factor or related molecule from the culture medium. In the case of culturing cells which require the absence of HLF from the culture medium, antagonists or antibodies of HLF described herein may be used to bind to and remove HLF from culture medium preparations thus resulting in "HLF-free" culture media.

Formulations

The HLF polypeptide composition will be formulated and dosed in a fashion consistent with good medical practice, taking into account the clinical condition of the individual patient (especially the side effects of treatment with HLF polypeptide alone), the site of delivery of the HLF polypeptide composition, the method of administration, the scheduling of administration, and other factors known to practitioners. The "effective amount" of HLF polypeptide for purposes herein is thus determined by such considerations.

As a general proposition, the total pharmaceutically effective amount of HLF polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the HLF polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the HLF of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The HLF polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release HLF polypeptide compositions also include liposomally entrapped HLF polypeptide. Liposomes containing HLF polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal HLF polypeptide therapy.

For parenteral administration, in one embodiment, the HLF polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the HLF polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The HLF polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of HLF polypeptide salts.

HLF polypeptide to be used for therapeutic administration must be sterile. Sterility is readily accomplished by filtration through sterile filtration membranes (e.g., 0.2 micron membranes). Therapeutic HLF polypeptide compositions generally are placed into a container having a sterile access port, for example, an intravenous solution bag or vial having a stopper pierceable by a hypodermic injection needle.

HLF polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous HLF polypeptide solution, and the resulting mixture is lyophilized. The infusion solution is prepared by reconstituting the lyophilized HLF polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of HLF on cells, such as its interaction with HLF-binding molecules such as receptor molecules. An agonist is a compound which increases the natural biological functions of HLF or which functions in a manner similar to HLF, while antagonists decrease or eliminate such functions.

In another aspect of this embodiment the invention provides a method for identifying a receptor protein or other ligand-binding protein which binds specifically to a HLF polypeptide. For example, a cellular compartment, such as a membrane or a preparation thereof, may be prepared from a cell that expresses a molecule that binds HLF. The preparation is incubated with labeled HLF. HLF and complexes of HLF bound to the receptor or other binding protein are isolated and characterized according to routine methods known in the art. Alternatively, the HLF polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds HLF, such as a molecule of a signaling or regulatory pathway modulated by HLF. The preparation is incubated with labeled HLF in the absence or the presence of a candidate molecule which may be a HLF agonist or antagonist. The ability of the candidate molecule to bind the binding molecule is reflected in decreased binding of the labeled ligand. Molecules which bind gratuitously, i.e., without inducing the effects of HLF on binding the HLF binding molecule, are most likely to be good antagonists. Molecules that bind well and elicit effects that are the same as or closely related to HLF are agonists.

HLF-like effects of potential agonists and antagonists may by measured, for instance, by determining activity of a second messenger system following interaction of the candidate molecule with a cell or appropriate cell preparation, and comparing the effect with that of HLF or molecules that elicit the same effects as HLF. Second messenger systems that may be useful in this regard include but are not limited to AMP guanylate cyclase, ion channel or phosphoinositide hydrolysis second messenger systems.

Another example of an assay for HLF antagonists is a competitive assay that combines HLF and a potential antagonist with membrane-bound HLF receptor molecules or recombinant HLF receptor molecules under appropriate conditions for a competitive inhibition assay. HLF can be labeled, such as by radioactivity, such that the number of HLF molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing HLF-induced activities, thereby preventing the action of HLF by excluding HLF from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of HLF. The antisense RNA oligonucleotide hybridizes to the mRNA in vivo and blocks translation of the mRNA molecule into HLF polypeptide. The oligonucleotides described above can also be delivered to cells such that the antisense RNA or DNA may be expressed in vivo to inhibit production of HLF protein.

The agonists and antagonists may be employed in a composition with a pharmaceutically acceptable carrier, e.g., as described above. The antagonists may be employed for instance to inhibit the binding to, and activation of, cell surface receptor molecules belonging to the erbB family, as well as other known or unknown cell surface receptor molecules. Consequently, inhibition of such receptor binding will result in the indirect inhibition of stimulation of the corresponding signal transduction pathways. Many of the corresponding signal transduction pathways are involved in the regulation of cell division and growth. The genesis or acceleration of many cancers resulting from other related or unrelated mechanisms is linked to abnormally increased levels of cell surface receptor molecule stimulation. The activity of an HLF antagonist will result in blocking an abnormally increased level of HLF activity, and, in turn, diminish an abnormally increased level of the stimulation of signal transduction pathways. This situation will ultimately result in a return to the normal regulation of cell division and growth and a corresponding diminution of the corresponding oncogenic state. Thus, HLF antagonists of the present invention may be employed to treat cancers. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a HLF protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "GST-Tagged" EGF-Like Domain of HLF in *E. coli*

The bacterial expression vector pGEX-3X was used for bacterial expression in this example (Pharmacia, Inc., Uppsala, Sweden). pGEX-3X encodes ampicillin antibiotic resistance ("Ampr") and contains a bacterial origin of replication ("ori"), an IPTG inducible promoter, and a sequence that encodes an N-terminal, in frame, glutathione S-transferase (GST) tag that allows affinity purification using one of the GST Purification Modules, and several suitable single restriction enzyme cleavage sites. These elements are arranged such that an inserted DNA fragment encoding a polypeptide expresses that polypeptide with an N-terminal GST-fusion protein.

The DNA sequence encoding the desired portion of the HLF protein comprising the EGF-like domain of the HLF amino acid sequence was amplified from the deposited cDNA clone using PCR oligonucleotide primers which annealed to the amino and carboxy terminal sequences of the desired portion of the HLF protein. Additional nucleotides containing restriction sites to facilitate cloning in the pGEX-3X vector were added to the 5' and 3' primer sequences, respectively. For cloning the EGF-like domain of the HLF protein, the 5' primer had the sequence 5' GGC GGATCCCTCTTCTTCCTCCTCC 3' (SEQ ID NO:5) containing the underlined Bam HI restriction site followed by 16 nucleotides of the amino terminal coding sequence of the EGF-like domain of the HLF sequence in SEQ ID NO:2. The 3' primer had the sequence 5' GGC GAATTCTAAACTTCTTCACTCTCCATGAATTCAATC-CCC 3' (SEQ ID NO:6) containing the underlined Eco RI restriction site followed by 33 nucleotides complementary to the 3' end of the EGF-like domain of the HLF DNA sequence in FIG. 1A.

The amplified HLF DNA fragment and the vector pGEX-3X were digested with Bam HI and Eco RI and the digested DNAs were then ligated together. Insertion of the HLF DNA into the restricted pGEX-3X vector placed the HLF protein coding region downstream from the IPTG-inducible promoter and in frame with an initiating AUG and the N-terminal GST fusion tag.

The ligation mixture was transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with ampicillin (100 μg/ml). The O/N culture was used to inoculate a large culture, at a dilution of approximately 1:25 to 1:250. The cells were grown to an optical density at 600 nm ("OD600") of approximately 0.4. Isopropyl-β-D-thiogalactopyranoside ("IPTG") was then added to a final concentration of 0.1 mM to induce transcription from the lac repressor sensitive promoter, by inactivating the lacI repressor. Cells subsequently were incubated further for 3 to 4 hours. Cells then were harvested by centrifugation, resuspended in 1×PBS, and lysed by sonication.

The expressed GST-HLF(EGF domain) fusion protein was purified using glutathione sepharose 4B essentially as described by the manufacturer (Pharmacia, Uppsala, Sweden). Briefly, cell lysates were combined with the glutathione sepharose 4B. The mixture was pelleted by centrifugation and washed. The GST fusion portion of the polypeptide was cleaved by the addition of thrombin site-specific protease for 18 hours. Following cleavage, thrombin was bound to p-Aminobenzmidine agarose beads. The thrombin-p-Aminobenzmidine agarose bead complexes and the GST-glutathione sepharose complexes were pelleted by centrifugation. The supernatant then contained the purified EGF domain of the HLF protein. Purity of the protein preparation was analyzed by SDS-PAGE. The purified protein was then stored frozen at −20° C.

Example 2

Cloning and Expression of HLF Protein in a Baculovirus Expression System

In this illustrative example, the plasmid shuttle vector pA2GP is used to insert the cloned DNA encoding the mature protein, lacking its naturally associated secretory signal (leader) sequence, into a baculovirus to express the mature HLF protein, using a baculovirus leader and standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as Bam HI, Xba I and Asp 718. The polyadenylation site of the simian virus 40 (SV40) is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the mature HLF protein in the deposited clone, lacking the AUG initiation codon and the naturally associated leader sequence shown in SEQ ID NO:2, is amplified using PCR oligonucleotide primers corresponding to the 5' and 3' sequences of the gene. The 5' primer has the sequence 5' GGC GGATCCCCTCTTCTTCCTCCTCC-3'. (SEQ ID NO:7) containing the underlined Bam HI restriction enzyme site followed by 16 nucleotides of the sequence of the mature HLF protein shown in SEQ ID NO:2, beginning with the indicated N-terminus of the extracellular domain of the HLF protein. The 3' primer has the sequence 5 GGC GGTACCTAAACTTCTTCACTCTCCATGAATTCAATC-CCC 3' (SEQ ID NO:8) containing the underlined Asp 718 restriction site followed by 33 nucleotides complementary to the 3' coding sequence in FIG. 1A.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Statagene Cloning Systems, La Jolla, Calif.) cells are transformed with the ligation mixture and spread on culture plates, Bacteria are identified that contain the plasmid with the human HLF gene by digesting DNA from individual colonies using Bam HI and Asp 718 and then analyzing the digestion product by gel electrophoresis. The sequence of the cloned fragment is confirmed by DNA sequencing. This plasmid is designated herein pA2GPHLF.

Five μg of the plasmid pA2GPHLF is co-transfected with 1.0 μg of a commercially available linearized baculovirus DNA ("BaculoGold™ baculovirus DNA", Pharmingen, San Diego, Calif.), using the lipofection method described by Feigner et al., *Proc. Natl. Acad. Sci. USA* 84: 7413–7417 (1987). One μg of BaculoGold™ virus DNA and 5 μg of the plasmid pA2GPHLF are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-HLF.

To verify the expression of the HLF gene Sf9 cells are grown in Grace's medium supplemented with 10% heat-inactivated FBS. The cells are infected with the recombinant baculovirus V-HLF at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the extracellular domain of the HLF protein.

Example 3

Cloning and Expression of HLF in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLV1, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pHLFHA, is made by cloning a portion of the cDNA encoding the extracellular domain of the HLF protein into the expression vector pcDNAI/Amp or pcDNAIII (which can be obtained from Invitrogen, Inc.). To produce a soluble, secreted form of the polypeptide, the extracellular domain is fused to the secretory leader sequence of the human IL-6 gene.

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the extracellular domain of the HLF polypeptide is cloned into the polylinker region of the vector so that recombinant protein expression is directed by the CMV promoter. The plasmid construction strategy is as follows. The HLF cDNA of the deposited clone is amplified using primers that contain convenient restriction sites, much as described above for construction of vectors for expression of HLF in *E. coli*. Suitable primers include the following, which are used in this example. The 5' primer, containing the underlined Bam HI site, a Kozak sequence, an AUG start codon, a sequence encoding the secretory leader peptide from the human IL-6 gene, and 16 nucleotides of the 5' coding region of the extracellular domain of the HLF polypeptide, has the following sequence: 5' GCC GGATCCGCCACCATGAACTCCTTCTCCACAAGCGC-CTTCGGTCCAGTTGCCTTCTC-CCTGGGGCTGCTCCTGGTGTTGCCTGCT-GCCTTCCCTGCCCCAGTCTCTTCTTCCTCCTCC 3' (SEQ ID NO:9). The 3' primer, containing the underlined Xba I and 33 of nucleotides complementary to the 3' coding sequence immediately before the stop codon, has the following sequence: 5' GGCTCTAGATAAACTTCTTCAC-TCTCCATGAATTCAATCCCC 3' (SEQ ID NO:10).

The PCR amplified DNA fragment and the vector, pcDNAI/Amp, are digested with Bam HI and Xba I and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the HLF polypeptide For expression of recombinant HLF, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of HLF by the vector.

Expression of the HLF-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of HLF polypeptide. Plasmid pC4 is a derivative of the plasmid pSV2-dhfr (ATCC Accession No. 37146). To produce a soluble, secreted form of the polypeptide, the extracellular domain is fused to the secretory leader sequence of the human IL-6 gene. The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology,* March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the HLF polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the extracellular domain of the HLF polypeptide is amplified using PCR oligonucleotide primers corresponding to the 5' and 3' sequences of the desired portion of the gene. The 5' primer containing the underlined Bam HI site, a Kozak sequence, an AUG start codon, a sequence encoding the secretory leader peptide from the human IL-6 gene, and 16 nucleotides of the 5' coding region of the extracellular domain of the HLF polypeptide, has the following sequence (where Kozak is in italics): 5' GCC<u>GGATCC</u>GCCACC*ATG*AACTCCTTCTC-CACAAGCGCCTTCGGTCCAGTTGCCT-TCTCCCTGGGGCTGCTCCTGGTGTTGC-CTGCTGCCTTCCCTGCCCCAGTCTCT-TCTTCCTCCTCC 3' (SEQ ID NO:9). The 3' primer, containing the underlined Asp 718 restriction site and 33 nucleotides complementary to the 3' coding sequence immediately before the stop codon as shown in FIG. 1A (SEQ ID NO:1), has the following sequence: 5' GGC<u>GGTACC</u>TAAACTTCTTCACTCTCCATGAATTCAATC-CCC 3' (SEQ ID NO:8).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of HLF mRNA Expression

Northern blot analysis is carried out to examine HLF gene expression in human tissues, using methods described by, among others, Sambrook et al., cited above. A cDNA probe containing the entire nucleotide sequence of the HLF protein (SEQ ID NO:1) is labeled with $^{32}p$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for HLF mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Example 5

Analysis of erbB Receptor Family Activation

To test for the ability of recombinant EGF domain of the HLF protein (as produced in Example 1) to activate erbB family members, a tyrosine kinase activation assay was used as follows. In this analysis, a human breast cancer cell line (MCF-7) was allowed to become quiescent by extended culture in low serum medium. Exogenous recombinant EGF domain of the HLF protein (10 mg.mL) or recombinant heregulin (0.1 mg.mL) were added to the growth medium, and cell culture was continued in the presence or absence of exogenous protein for 30 minutes. Cells were harvested and lysed by the addition of SDS-containing sample buffer (1% SDS, 0.15M Tris, pH 8.6, 5% BME, and 1 mM sodium ortho-vanadate).

Cell lysates were then subject to SDS-PAGE on 16–20% Tris-glycine gradient gels (Novex). Subsequently, electrophoretically separated proteins were transferred to a Hybond ECL nitrocellulose membrane (Amersham). Tyrosine phosphate containing proteins were identified by immunoblotting using anti-phosphotyrosine antibodies.

Figure 4:
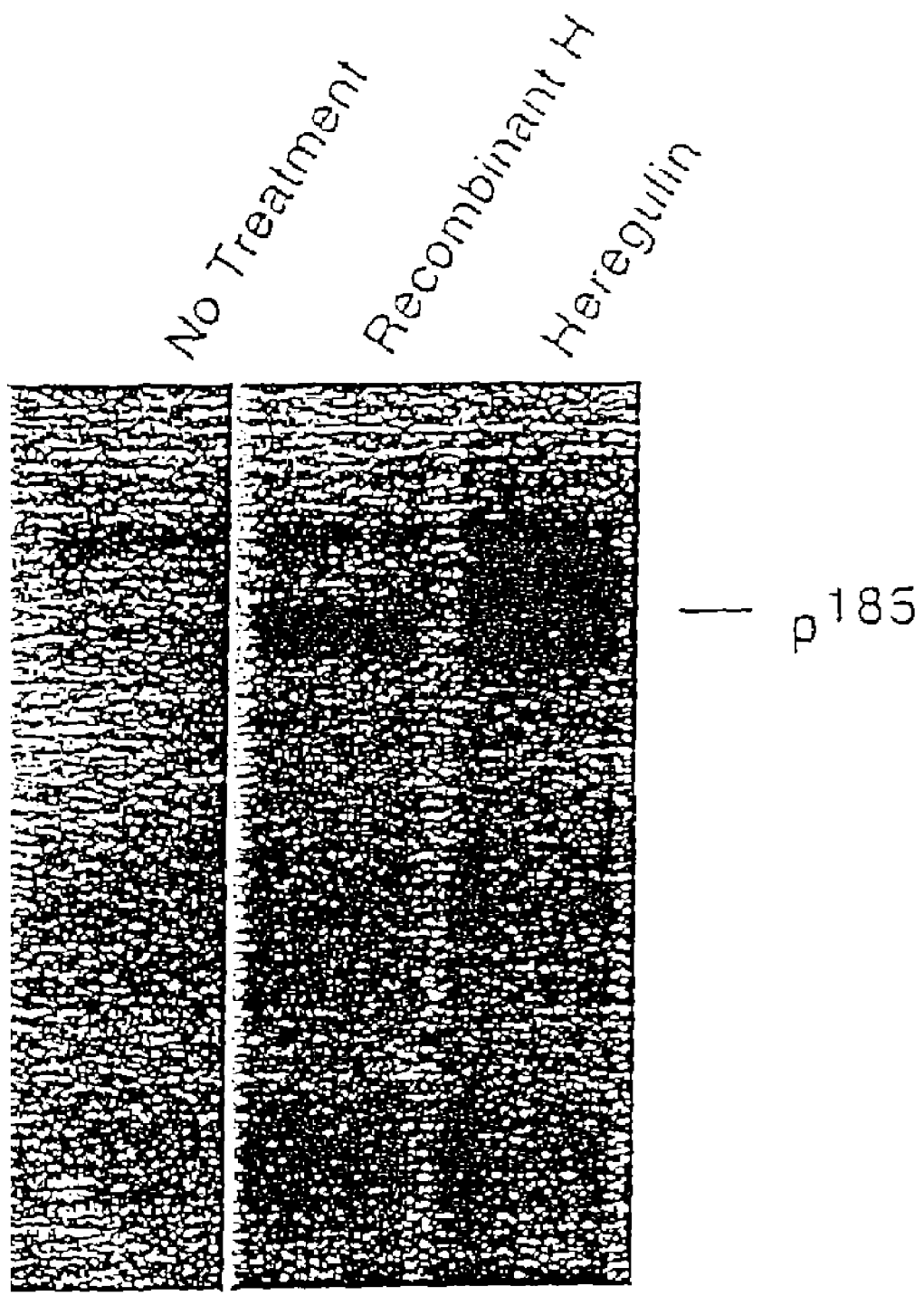
FIG. 4 shows a demonstration of the biochemical activity of a recombinant EGF domain of the HLF protein (designated "H" in the figure; as described in Example 5). The figure shows a Western blot of MCF-7 cell lysates prepared from cultures which were treated or mock-treated with recombinant EGF domain of the HLF protein or with recombinant heregulin. The blots were immunoblotted with an anti-phosphotyrosine monoclonal antibody.

As shown in FIG. 4, there is a clear increase in the tyrosine phosphorylation of proteins in the size range of approximately 185 kDa in samples prepared from cultures which were grown in medium which contained the recombinant EGF domain of the HLF protein. The erbB family of cell surface receptor molecules consists of at least four members, all of which are roughly the molecular mass of the proteins observed to increase in tyrosine phosphorylation in this analysis. Furthermore, treatment of MCF-7 cells with recombinant heregulin in this analysis produced a similar result with regard to a change in the tyrosine phosphorylation state of cellular proteins.

These results strongly suggest that recombinant EGF domain of the HLF protein was able to activate phosphorylation of at least one of the members of the erbB family of cell surface receptors expressed in these cells.

Example 6

HLF in Breast Cancer Cells, Activation of Multiple erbB Proteins

Introduction

Increased activity of members of the erbB family has been implicated in the development of cancer. Different molecular mechanisms of activation have been identified. The ligands of the EGF/Heregulin family are inappropriately expressed in breast cancers. EGF, alpha-TGF, amphiregulin and heregulin are expressed in breast cancers containing appropriate receptors thus leading to autocrine growth stimulation. The importance of autocrine growth stimulation is required for the transformation of NIH/3T3 cells with high levels of EGF receptor, since full morphological transformation requires the co-expression of alpha-TGF. The causative role of autocrine growth stimulation by alpha-TGF in breast cancer is demonstrated in experiments using transgenic animals where the expression of alpha-TGF acts synergistically to produce frequent breast cancers. These findings indicate that the co-incident expression of erbB receptor proteins with their ligands can result in aberrant cell growth. Moreover, in 20% of breast cancers amplification of the erbB2 gene results in overexpression of p185erb$^{B-2}$. In these cancers activation of signalling has been thought to be independent of ligand activation. Overexpression of p185erb$^{B-2}$ is an oncogenic event in experimental systems. To date no ligand has been isolated that binds only to erbB2. However, recent studies show that erbB2 can form part of a receptor for heregulin. Overexpression of the erbB1 (EGFR) protein is common, although gene amplification is infrequent in breast cancer.

The erbB receptors bind their ligands as dimers—formed from two identical erbB proteins (homodimers) or from two different proteins (heterodimers). EGF can bind homodimers of erbB1 (EGFR) or heterodimers of erbB1 and erbB2. Similarly, Heregulin1b can bind homodimers of erbB4 or heterodimers of erbB2 and erbB3. Other ligands of the EGF/Heregulin family have receptors formed by homo and heterodimers of erbB proteins. Ligand binding and dimer formation leads to increased autophosphorylation of the receptor proteins and substrates activating intracellular signalling pathways.

The cellular consequences of receptor stimulation by members of the EGF/Heregulin family vary with the ligand and cellular context. EGF and alpha-TGF can stimulate the growth of many cells in culture, but in cases of breast cancers that overexpress the EGF Receptor, EGF can be growth inhibitory at concentrations above approximately 10 nM. In a similar way, heregulin can both stimulate growth of some human cancer cells as well as inhibit those that overexpress erbB2. The display of erbB proteins on breast cancer cells is not uniform. Many cells lack one or more of the family and others greatly overexpress erbB1 or erbB2. Heregulin clearly has effects on cell morphology as evidenced by changes in the actin cytoskeleton. Heregulin seems to play a number of specialized roles in appropriate regulation the neuro-muscular junction, between neuronal and glial cells and in Schwann cell development. In prenatal development heregulin and erbB2 and erbB4 control in morphogenesis of brain and heart. These findings indicate that members of the EGF/Heregulin family can have: differing effects on cell phenotype.

In this study we characterize a new ligand for the EGF/Heregulin family of growth factors. Our results indicate that HLF binds and activates multiple members of the erbB family of receptors. We demonstrate that HLF is expressed in a human breast cancer cell line and can alter the growth of human breast cancer cell lines. These results indicate that HLF may have in vivo effects on the growth of the normal and malignant breast epithelial cells.

Results

HLF contains an EGF like domain.

The ligands of the EGF/Heregulin family have a well-defined sequence similarity which we used to identify HLF. FIG. 5 shows a compilation of known ligands of the EGF/Heregulin family; all contain 6 cysteines. Between the fourth and sixth cysteine is the common EGF-like folding motif containing a conserved hydrophobic amino acid (Y37 (Tyr-68 of SEQ ID NO:2)) and a conserved glycine (G39 (Gly-70 of SEQ ID NO:2)). This region apparently forms a very stable core structure that is used in many extracellular proteins. Sequence similarity among the ligands is not limited to this folding motif. There is an exactly conserved arginine (R41 (Arg-72 of SEQ ID NO:2)) and hydrophobic amino acids at positions 14 and 16 (Asn-45 and Asp-46 of SEQ ID NO:2). A hydrophobic amino acid that is required for binding activity is found at position 46 or 47 (Leu-77 or Pro-78 of SEQ ID NO:2). The number of amino acids between cysteines is similar among the ligands with the notable exception of loop B and loop C. Heregulins have a loop C which is three amino acids longer than the EGF-like ligands. The overall sequence similarity among the EGF/Heregulin family members is 19–42% (except between Hrg1a and Hrg1b which are derived from the same gene). Recently, NRG2 has been identified in rat brain. NRG2 is most closely related to Hrg1b with sequence identity of 42% in the EGF like domain.

Using a consensus sequence derived from EGF and Heregulin sequences we screened the HGS database of over 800,000 sequences. As shown in FIG. 5, one cDNA encoded the HLF sequence which has 34–38% similarity to EGF and Heregulin Family within the EGF-like domain. Importantly, in the HLF sequence, all of the conserved cysteine residues, the R41, and the G39 (Gly-70 and Arg-72 of SEQ ID NO:2, respectively) are exactly conserved. There is additional sequence conservation in NRG-3, notably hydrophobic amino acids at positions 13, 15, 37 and 46–47 (Leu-44, Asp-46, Tyr-68, and Leu-77-Pro-78 of SEQ ID NO:2, respectively). The length of the B and C loops are more similar to heregulin than EGF. Within the coding frame defined by our current cDNA clone there is a sequence of hydrophobic amino acids that is consistent with a transmembrane domain C-terminal to the EGF-like domain. This structure is similar to the transmembrane domains found in alpha-TGF, EGF, heregulin and other ligand precursor proteins (not shown in FIG. 5). The sequence attributes of the HLF cDNA make it a strong candidate as encoding a novel growth factor binding one or several of the erbB family of receptors. NGR-2 is 36% identical to HLF in the highly conserved EGF-like domain therefore they are products of distinct genes. Don-1 has also been recently and independently identified by sequence similarity to EGF/Heregulin and is apparently the product of the same gene as NRG-2.

Demonstration that HLF activates erbB Family Proteins.

In order to obtain an initial estimation for the action of HLF as a ligand for erbB family of receptors we generated recombinant protein in *E. coli* using a GST fusion system (see also Example 1). The EGF-like domain of HLF was released and purified from the GST by thrombin cleavage. The resulting protein contained a single polypeptide when analyzed by SDS-PAGE.

To test for the ability of recombinant HLF to activate receptors of the erbB family we used a tyrosine kinase activation assay. Tyrosine phosphate containing proteins were then identified by immunoblotting using anti-phosphotyrosine antibodies. We found a clear increase in the tyrosine phosphorylation at ~p185 when recombinant HLF is applied to MCF-7. In MCF-7 cells recombinant heregulin-1b results in a large increase in tyrosine phosphorylated proteins at about this size. These results indicate that recombinant HLF is able to activate phosphorylation of at least one of the members of the erbB family expressed in MCF-7 cells.

HLF Activates Multiple erbB Proteins.

In order to begin the analysis of the HLF receptor we used an experimental system where the display of erbB proteins can be controlled. The 32D cell is a murine myeloid cell line which is devoid of expression of genes of the erbB family. Growth of 32D cells is dependent on the IL-3 present in WEHI conditioned media. When expression constructs encoding an erbB protein are introduced into 32D cells the resulting cell can survive in the absence of IL-3 if an appropriate EGF/Heregulin family member is present. For example, the introduction of EGF Receptor expression leads to growth of 32D cells in the presence of EGF or alpha-TGF and introduction of erbB4 allows growth in heregulin. Similar experimental systems have been used to examine the receptor specificity of the newly discovered NRG-2. We also show that growth of 32D cells in the presence of HLF occurs only when EGF Receptor or erbB4 are present singly or when erbB2 and erbB3 are present in combination. The expression of erbB2 or erbB3 alone does not lead to HLF induced growth. To confirm that this growth stimulation was the result of receptor activation we determined whether HLF induces the tyrosine phosphorylation of EGF Receptor, erbB4 or erbB2 and erbB3 when expressed together. We show the appearance of an appropriate sized band when cell lysates of these 32D cells are probed by antiphosphotyrosine antibodies. These results are strong evidence that HLF can activate erbB1 homodimers (the EGF receptor), erbB4 homodimers, and erbB2+erbB3 heterodimers.

The results of 32D experiments indicate that the receptor binding pattern of HLF is complex. In order to confirm that HLF activates proteins other than erbB4 in MCF-7 cells we immunoprecipitated erbB3 and determined the level of tyrosine phosphorylation by immunoblot. We also observed that erbB3 is phosphorylated on tyrosine as a consequence of HLF stimulation.

Biological Activity of HLF.

The effects of the EGF/Heregulin family vary significantly. Differing cellular phenotypes can be induced by different ligands in the same cell system and the same ligand can cause differing effects among different cells. Mitogenic activity of HLF has been detected in 32D cell experiments. The MCF-7 cell is dependent on estrogens in the media either in the form of phenol red or present in the fetal bovine serum. Little proliferation is seen in phenol red free media containing serum treated with charcoal to remove steroids. Heregulin is able to promote growth in the absence of estrogen. When HLF is added there is also a clear growth stimulation. Growth inhibitory effects have also been observed. HLF inhibits the growth of the breast cancer cell line MDA-MB-468. These cells overexpress the EGF receptor and can be stimulated by EGF at low concentrations (<10 nM) and growth inhibited at higher concentrations (>10 nM). HLF was found to inhibit growth of MDA-MB-468 under conditions similar to those producing growth stimulation of 32D cells containing EGF Receptor. No growth suppression or stimulation are seen when HLF is applied to MCF-7 cells when they are grown in media containing agonists for the estrogen receptor.

HLF mRNA Expression in Breast Cancer.

Preliminary experiments using northern blotting methods showed a weak signal for HLF mRNA in adult brain with a size of approximately 2 kD (data not shown). Similar northern blot results are reported in the recent HLF study. Because of the weakness of this signal we have used RT-PCR to detect HLF mRNA. We have confirmed expression in the brain and detect equivalent signals in samples of normal and breast cancer tissue. RT-PCR employed two primer sets. The two primer sets generated concordant results. This indicates that the bands observed by RT-PCR were due to actual HLF mRNA. In addition all assays included control reactions lacking reverse transcriptase in order to detect the presence of contaminating DNA. The observed band at 340 bp corresponds to the predicted size based on the HLF cDNA. It was cloned sequenced and shown to contain HLF coding information. Bands at 500 bp and 120 bp were also sequenced. These do not contain HLF coding information and thus likely represent mispriming by the RT-PCR oligonucleotides on unrelated mRNAs. These results are strong evidence that HLF can be expressed in human breast cancer cell lines.

Discussion

Our results suggest that HLF can bind and activate erbB1 and heterodimers of erbB2+erbB3. Taken together the available data suggests that the precise receptor binding and activation profile of HLF is complex. Our results demonstrate that erbB3 can be phosphorylated as a consequence of HLF binding. The HLF induced increases in tyrosine phosphorylation on erbB3 suggests that the erbB3 protein can be part of an HLF receptor. Our studies of 32D cells supports this conclusion where erbB2 is the other member of the heterodimeric receptor with erbB3. Still to be determined is whether HLF can bind to erbB1+erbB3 heterodimers or erbB3+erbB4 heterodimers or erbB2+erbB4 heterodimers. Our preliminary data does conclusively demonstrate that HLF is a new ligand for the erbB family of receptors. These results suggest that HLF may have a receptor specificity somewhat analogous to b-cellulin.

In adult tissue expression levels of HLF are low but detectable using sensitive methods such as RT-PCR. HLF is expressed at the highest levels in brain where it is likely to play a critical role in morphogenesis. Interestingly, we identify HLF expression a breast cancer cell line, MCF-7, that clearly has receptors that can be activated by HLF. Our results also show that HLF can cause alteration of growth of MCF-7 cancer cells in vitro. The ability to cause growth of MCF-7 cells in the absence of estrogen is similar to that previously reported for heregulin. Our results suggest that effects on cell phenotype by HLF may depend on the cell line. MDA-MB-468 which has high levels of EGFR are growth inhibited by HLF in vitro.

The results in this paper together with those recently reported earlier identify HLF as a new ligand for the erbB family of growth factor receptors and suggest a role for HLF in the growth regulation of normal and malignant breast epithelial cells.

Materials and Methods

Preparation of Recombinant HLF. Preparation of recombinant HLF is also described in Example 1. In the case of the protein produced in this Example, the coding segment containing the EGF-like domain of HLF (nucleotide 79 to 279 of HGS38) were amplified by PCR and inserted into the pGEX3 plasmid for expression as a fusion protein with bacterial glutathione S transferase. Protein was prepared using standard methods. Bacteria were cultured to an $OD_{600}$ of approximately 0.4 and induced to express recombinant protein by addition of 0.1 mM IPTG. Bacteria were collected by centrifugation resuspended in 1×PBS and lysed by sonication. Recombinant protein was collected by incubation with glutathione beads. After washing the recombinant HLF protein was cleaved from the GST bound to the beads by thrombin cleavage for 18 hours. Thrombin was removed by incubation with p-Aminobenzamidine agarose beads. Refolding followed the methods used for the preparation of recombinant antibody fragments. Briefly, recombinant HLF was denatured in 6 M guanidine HCL containing 65 mM DTE. This was rapidly diluted 100 fold to a final protein concentration of 100 µg/ml into 0.4 M Arginine, 0.1 M Tris pH 8.0, 0.9 mM oxidized glutathione 2.0 mM EDTA. Refolding was allowed to proceed for 24 hours at 4° C. Refolded protein was extensively dialyzed against PBS using 3000 kDa cutoff membranes. Protein preparations were stored at −20° C.

Detection of Receptor Activation by Phosphotyrosine Immunoblot.

Cells were starved (24 hours for MCF-7, 4 hours for 32D derived cell lines) before addition of the indicated amounts of growth factors. Total cell lysates were prepared by addition of SDS PAGE sample buffer (1% SDS, 0.15M Tris pH 8.6, 5% BME and 1 mM Sodium Ortho Vanadate) directly to cells. Cell lysates and were run on 8–16% Tris-Glycine gradient gels (Novex). Proteins were transferred onto Hybond ECL nitrocellulose membranes (Amersham) and were immunoblotted with anti-phosphotyrosine MAb.

32D Cell Experiments.

32D cells containing expression constructs for erbB1, erbB2, erbB3, erbB4 and erbB2 and erbB3 together were grown in IL-3 containing (WEHI conditioned media) or HRG-1-beta prior to the experiment. Expression of the erbB proteins was verified by FACS analysis using erbB-specific antisera. Cells ($10^4$ per well) were plated in 24 well dishes in the absence of IL-3 containing media (DMEM, 10% FCS) or in the presence of the indicated growth factors, heregulin-1beta (100 ng/ml), EGF (100 ng/ml), and HLF (10 µg/ml). Cells were allowed to grow for 3 days and viable cells counted using a hemocytometer.

Immunoprecipitation and Immunoblot of erbB3.

Cells were plated in 80 cm² dishes (DMEM+10% FCS) for until 80% confluent. Cells were then allowed to become quiescent in serum free media (DMEM) for 24 hours. Cells were then stimulated with the indicated growth factors, heregulin-1beta (1 µg/ml), and HLF (10 µg/ml) for 15 minutes. Cells were lysed in 1% Triton X100 in PBS containing 1 mM Sodium orthovanadate. Nuclei were removed by centrifugation. erbB3 proteins were immunoprecipitated (2 hours at 40° C.) using monoclonal anti-erbB3 antibodies (Neomarkers) and collected on protein A sepharose. Proteins were released by incubation in 1% SDS containing PAGE sample buffer at 100° C. and electrophoresed on 8–16% gels (Novagen). Proteins were transferred to nitrocellulose. Proteins containing pTyr were detected using monoclonal anti-phosphotyrosine antibodies (Oncogene Science) and the ECL detection system (Amersham).

Growth Assays.

Cells were plated in IMEM+10% FBS at 3000 cells per well in 96 well dishes. Cells were allowed to become quiescent in serum free IMEM for 24 hours and growth factors EGF (2 ng/ml) and HLF (10 µg/ml) were added to the media. Growth of cells at 1, 3, and 5 days was monitored using the XTT assay method. XTT was added at 10 µg/ml in IMEM and PMS (1.5 mg/ml in PBS) to 25% of volume of well for 4 hours at 37° C. OD monitored at 540 nm.

Detection of HLF mRNA.

Total RNA was extracted from cultured cells using the RNazolB method (Tel-Test, CS-104). The final RNA pellet was resuspended in 135 µl DEPC treated $H_2O$. DNase treatment was performed using the SNAP RNA isolation kit (Invitrogen, K1950-01). Briefly, 10× DNase buffer and RNase free DNase I was added to each sample and incubated for 20 min at 37° C. RNA purification was performed as indicated in the kit. Concentration of each sample was determined, samples were dried and resuspended to give a final concentration of 2 µg/ul.

RT-PCR was performed using 2 µg of total RNA in the Gene Amp RNA PCR Core kit (Perkin Elmer, N808-0143). cDNA was synthesized using the downstream primer 5'-CCA CGA TGA CAA TTC CAA AG-3' (SEQ ID NO:20). Samples were reverse transcribed 1 h at 37° C. RT was heat inactivated 5 min at 99° C., samples were cooled on ice. PCR was performed with the entire RT reaction using the upstream primer 5'-TAC CAC CAC CAC ACC AGA AA-3' (SEQ ID NO:21). The reaction was performed for 40 cycles, 1 min at 94° C., 1 min 30 sec at 58° C., 2 min at 72° C. followed by an extension for 8 min at 72° C. Samples were electrophoresed on an agarose gel and visualized with ethidium bromide staining.

Confirmation of the sequence of the bands was performed by purifying the bands from agarose gel slices (Wizard PCR preps DNA purification system, Promeoa, A7170) and cloning into a TA vector (Invitrogen, K2000-JIO) for automated sequencing. Bands of unknown identity present in the reaction products were cloned and sequenced in a similar fashion.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, manuscripts, laboratory manuals, books, or other documents) cited herein are hereby incorporated by reference.

What is claimed is:

1. An isolated antibody or fragment thereof that specifically binds to a protein selected from the group consisting of:
    (a) a protein whose amino acid sequence consists of amino acid residues 1 to 157 of SEQ ID NO:2;
    (b) a protein whose amino acid sequence consists of amino acid residues 1 to 101 of SEQ ID NO:2;
    (c) a protein whose amino acid sequence consists of amino acid residues 26 to 93 of SEQ ID NO:2;
    (d) a protein whose amino acid sequence consists of a portion of SEQ ID NO:2, wherein said portion is at least 30 contiguous amino acid residues in length; and
    (e) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 1 that specifically binds protein (e).

7. The antibody or fragment thereof of claim 3 wherein said protein bound by said antibody or fragment thereof is glycosylated.

8. The antibody or fragment thereof of claim 3 wherein said antibody or fragment thereof is polyclonal.

9. The antibody or fragment thereof of claim 3 wherein said antibody or fragment thereof is monoclonal.

10. The antibody or fragment thereof of claim 3 which is selected from the group consisting of:
    (a) a chimeric antibody or fragment thereof; and
    (b) a Fab fragment.

11. The antibody or fragment thereof of claim 3 which is labeled.

12. The antibody or fragment thereof of claim 3 wherein said antibody or fragment thereof specifically binds to said protein in a Western blot or an ELISA.

13. An isolated cell that produces the antibody or fragment thereof of claim 3.

14. A hybridoma that produces the antibody or fragment thereof of claim 3.

15. An isolated antibody or fragment thereof that specifically binds a protein purified from a cell culture wherein said protein is encoded by a polynucleotide encoding amino acids 1 to 157 of SEQ ID NO:2.

16. The antibody or fragment thereof of claim 15 wherein said antibody or fragment thereof is monoclonal.

17. The antibody or fragment thereof of claim 15 wherein said antibody or fragment thereof is polyclonal.

18. The antibody or fragment thereof of claim 15 which is selected from the group consisting of:
    (a) a chimeric antibody or fragment thereof; and
    (b) a Fab fragment.

19. The antibody or fragment thereof of claim 15 wherein said antibody or fragment thereof specifically binds to said protein in a Western blot or an ELISA.

20. The antibody or fragment thereof of claim 15 wherein the amino acid sequence of said protein consists of amino acid residues 1 to 157 of SEQ ID NO:2.

* * * * *